(12) United States Patent
Gillard et al.

(10) Patent No.: US 8,475,504 B2
(45) Date of Patent: Jul. 2, 2013

(54) METHOD OF BONE FIXATION WITH SLENDER SPANNING MEMBERS DISPOSED OUTSIDE BONE

(75) Inventors: Joel Gillard, Portland, OR (US);
Randall J. Huebner, Portland, OR (US);
Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 862 days.

(21) Appl. No.: 12/175,223

(22) Filed: Jul. 17, 2008

(65) Prior Publication Data

US 2009/0069851 A1    Mar. 12, 2009

Related U.S. Application Data

(60) Provisional application No. 60/961,317, filed on Jul. 19, 2007.

(51) Int. Cl.
*A61B 17/70* (2006.01)
*A61B 17/04* (2006.01)

(52) U.S. Cl.
USPC .............. 606/281; 606/71; 606/287; 606/301

(58) Field of Classification Search
USPC ............... 606/60, 70, 71, 278, 280–287, 289, 606/291
See application file for complete search history.

(56) References Cited

U.S. PATENT DOCUMENTS

| | | |
|---|---|---|
| 2,501,978 A | 3/1950 | Wichman |
| 3,997,138 A | 12/1976 | Crock et al. |
| 5,190,545 A | 3/1993 | Corsi et al. |
| 5,665,088 A | 9/1997 | Gil et al. |
| 5,665,089 A | 9/1997 | Dall et al. |
| 5,697,934 A | 12/1997 | Huebner |
| 5,704,936 A | 1/1998 | Mazel |
| 5,810,824 A | 9/1998 | Chan |
| 5,827,286 A * | 10/1998 | Incavo et al. ................ 606/71 |
| 5,931,839 A | 8/1999 | Medoff |
| 5,941,878 A | 8/1999 | Medoff |
| 5,993,452 A | 11/1999 | Vandewalle |
| 6,096,040 A | 8/2000 | Esser |
| 6,117,160 A | 9/2000 | Bonutti |
| 6,228,087 B1 | 5/2001 | Fenaroli et al. |
| 6,312,431 B1 | 11/2001 | Asfora |
| 6,338,734 B1 | 1/2002 | Burke et al. |
| 6,348,052 B1 | 2/2002 | Sammarco |
| 6,506,191 B1 | 1/2003 | Joos |

(Continued)

FOREIGN PATENT DOCUMENTS

DE    42 01 531 A1    7/1993
DE    101 25 092 A1    12/2001

(Continued)

OTHER PUBLICATIONS

FixClip™ System, Current Methods in Fixation of Osteoporotic Bone, Chapter 6, p. 93, author unknown, undated.
U.K. Intellectual Property Office, U.K. Patent Application Serial No. GB0813210.2, Patents Act 1977: Search Report under Section 17; search date: Oct. 16, 2008.

*Primary Examiner* — David Isabella
*Assistant Examiner* — Marcia Hoffman
(74) *Attorney, Agent, or Firm* — Kolisch Hartwell, P.C.

(57) ABSTRACT

System, including methods, apparatus, kits, and components, for bone fixation using a pair of slender spanning members to span a fracture outside bone.

22 Claims, 10 Drawing Sheets

U.S. PATENT DOCUMENTS

| | | |
|---|---|---|
| 6,514,274 B1 | 2/2003 | Boucher et al. |
| 6,520,965 B2 | 2/2003 | Chervitz et al. |
| 6,682,533 B1 | 1/2004 | Dinsdale et al. |
| 6,712,820 B2 | 3/2004 | Orbay |
| 6,736,819 B2 | 5/2004 | Tipirneni |
| 7,037,308 B2 | 5/2006 | Medoff |
| 7,637,928 B2 * | 12/2009 | Fernandez .................. 606/289 |
| 2002/0143336 A1 | 10/2002 | Hearn |
| 2002/0193796 A1 | 12/2002 | Emidio |
| 2004/0097942 A1 | 5/2004 | Allen et al. |
| 2004/0210220 A1 | 10/2004 | Tornier |
| 2004/0225291 A1 | 11/2004 | Schwammberger et al. |
| 2005/0010228 A1 | 1/2005 | Medoff |
| 2005/0021087 A1 | 1/2005 | Koseki |
| 2006/0058796 A1 * | 3/2006 | Hartdegen et al. .............. 606/69 |
| 2006/0217722 A1 * | 9/2006 | Dutoit et al. .................... 606/69 |
| 2006/0235407 A1 | 10/2006 | Wang et al. |
| 2006/0276795 A1 | 12/2006 | Orbay et al. |

FOREIGN PATENT DOCUMENTS

| | | |
|---|---|---|
| DE | 102 26 074 A1 | 1/2003 |
| EP | 0 019 062 | 6/1983 |
| FR | 74 39762 | 7/1976 |
| GB | 2 331 244 A | 5/1999 |
| GB | 2 451 187 A | 1/2009 |
| WO | 2004091367 A3 | 10/2004 |

* cited by examiner

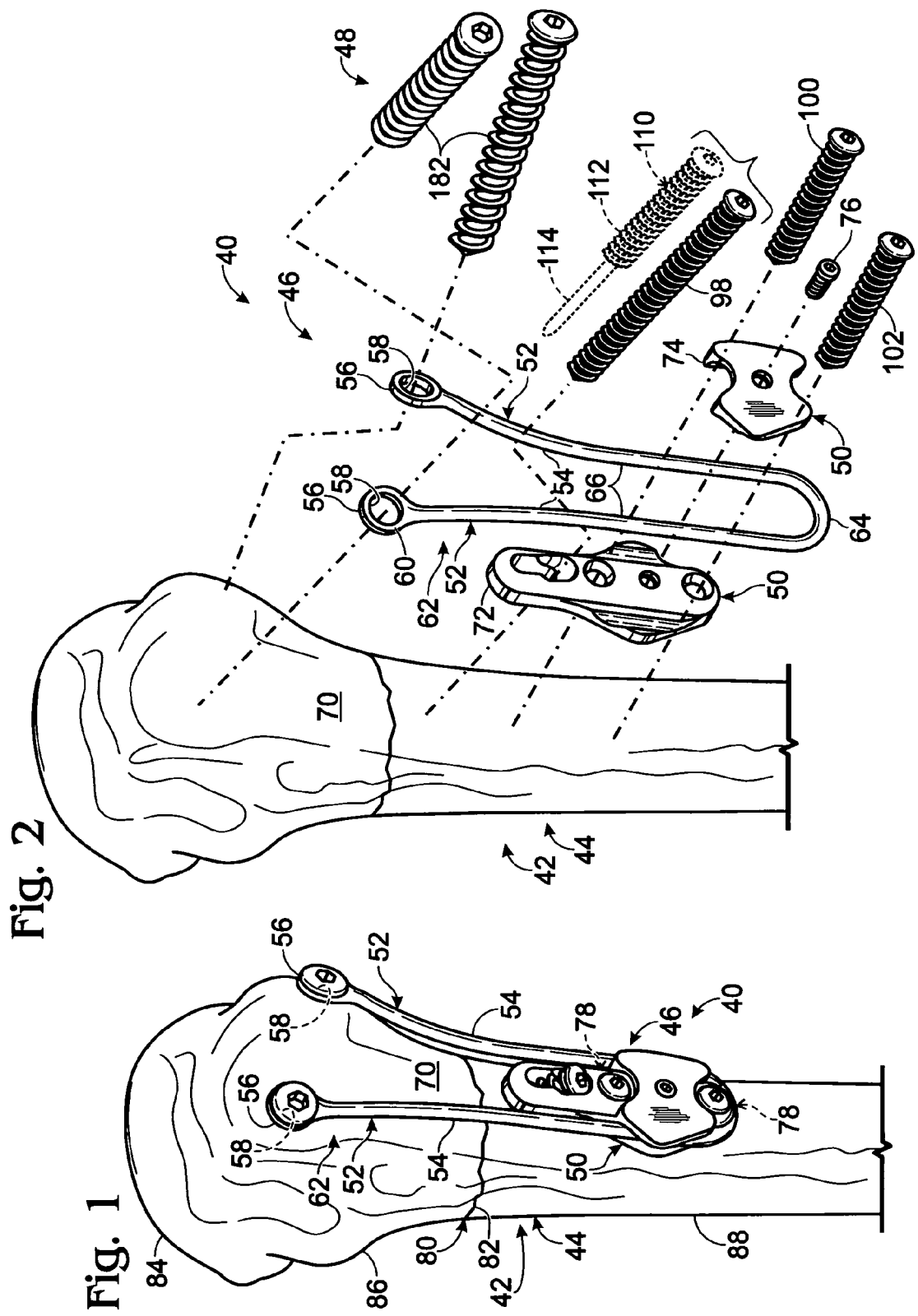

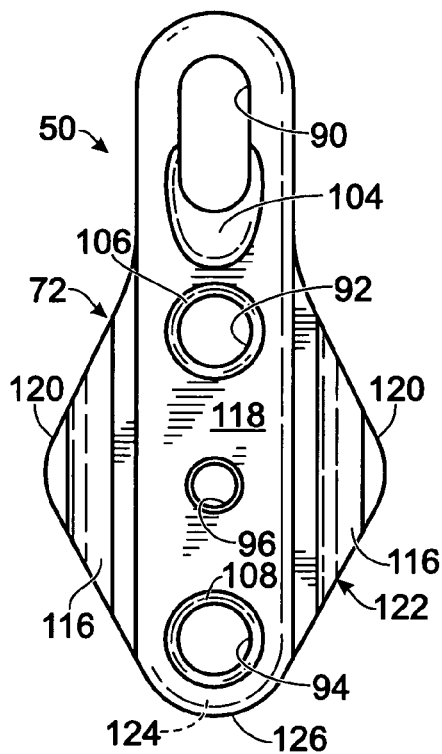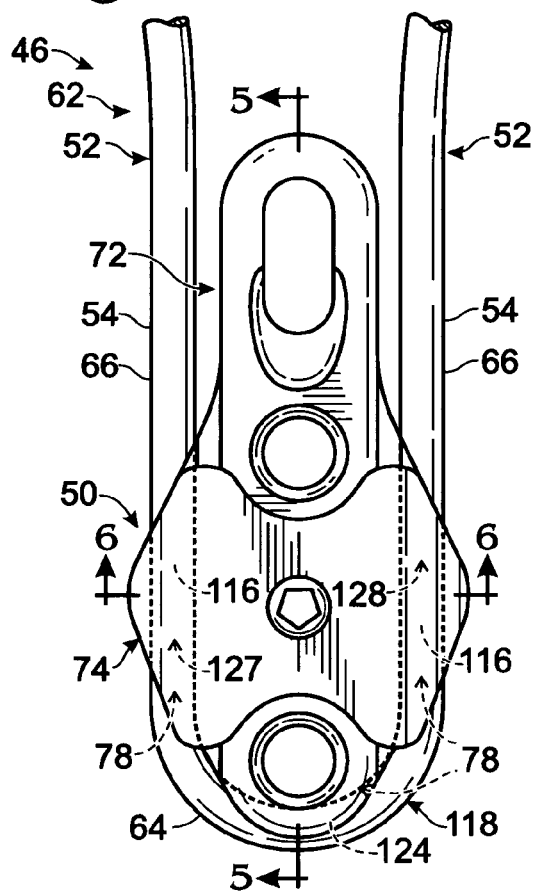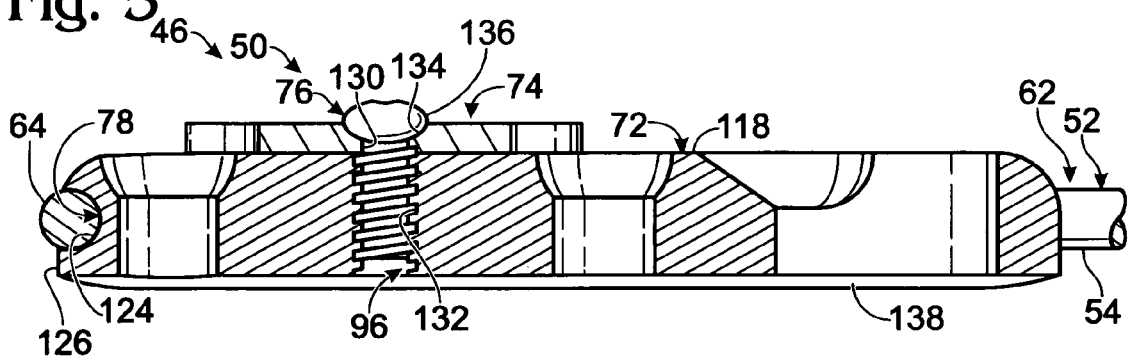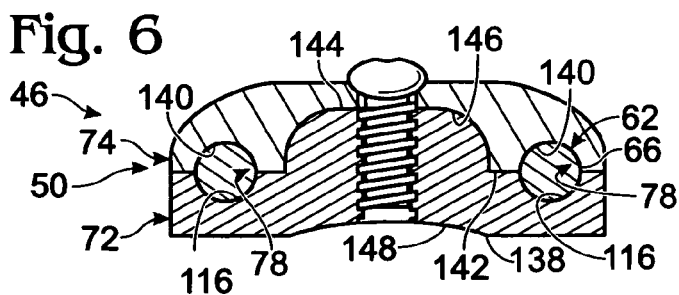

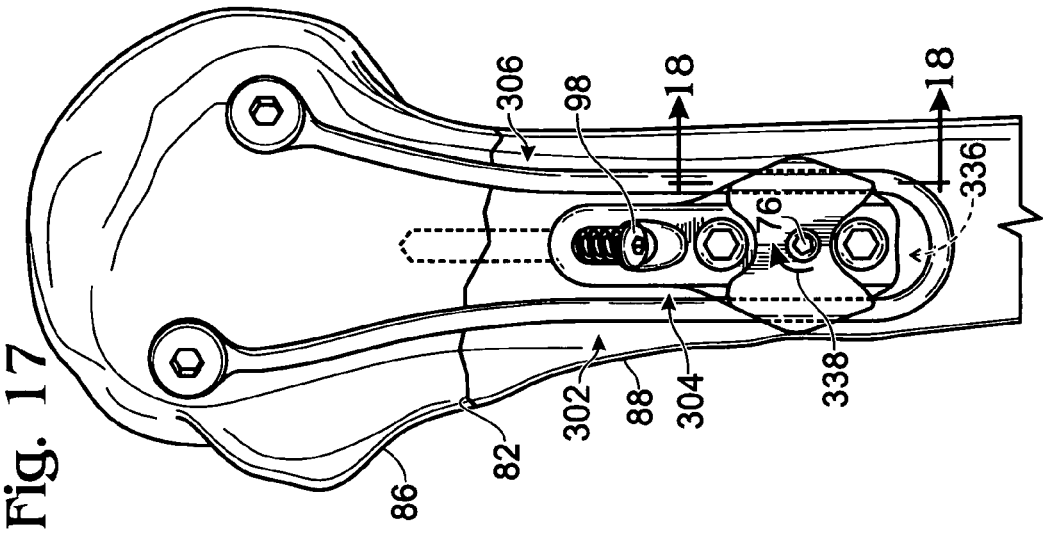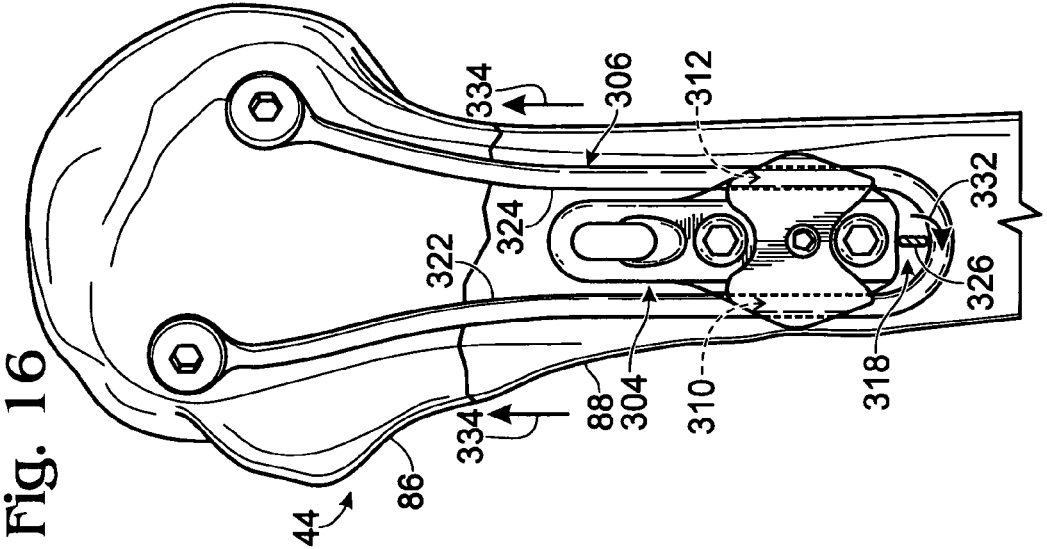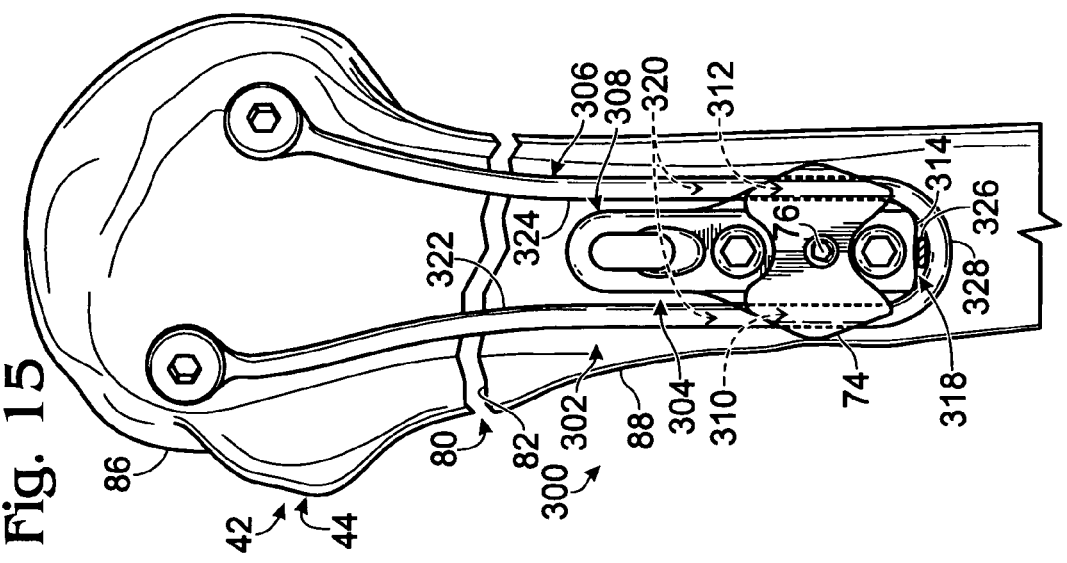

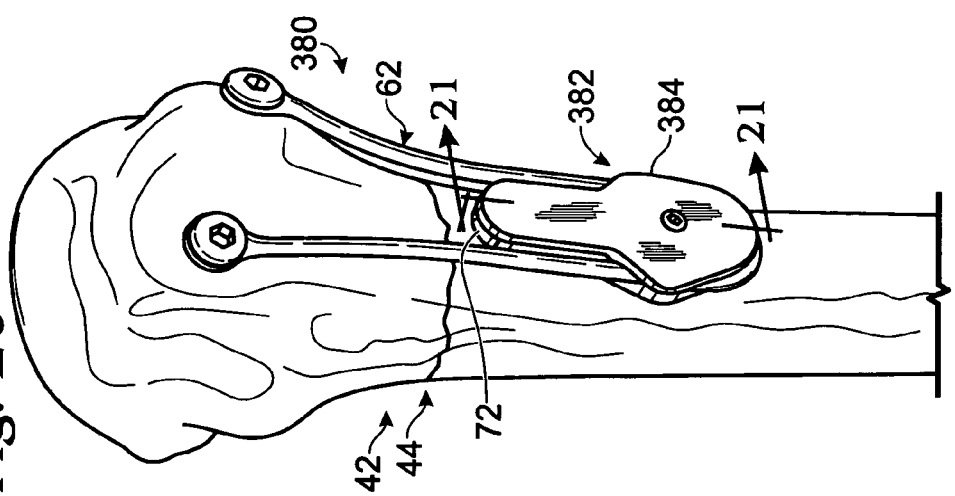
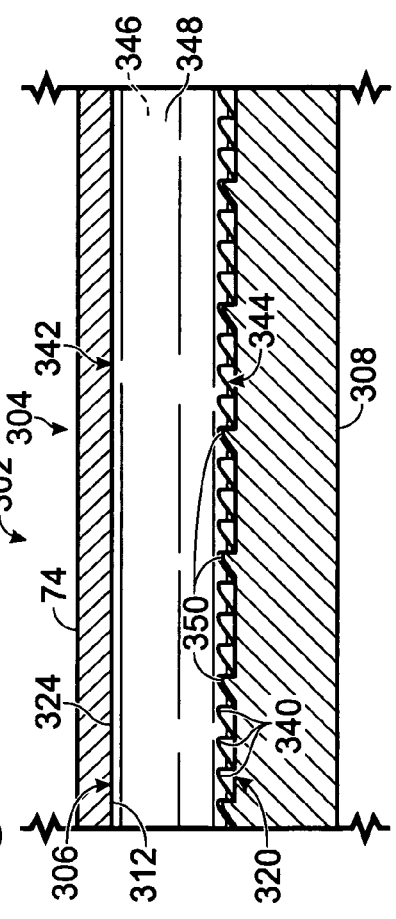
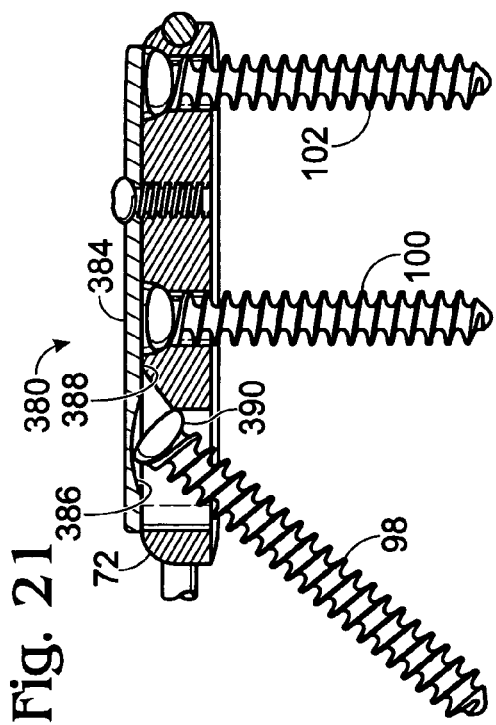
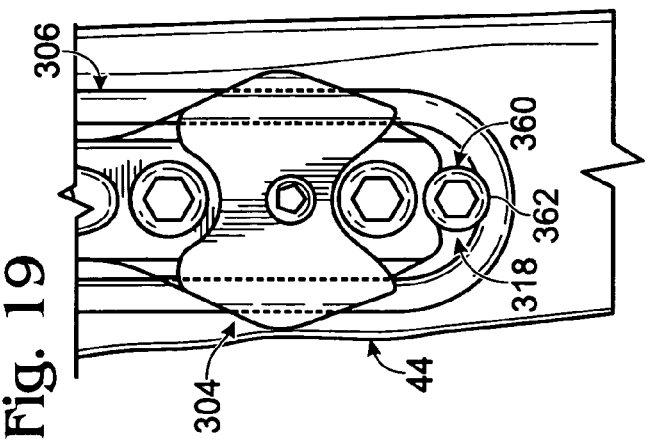

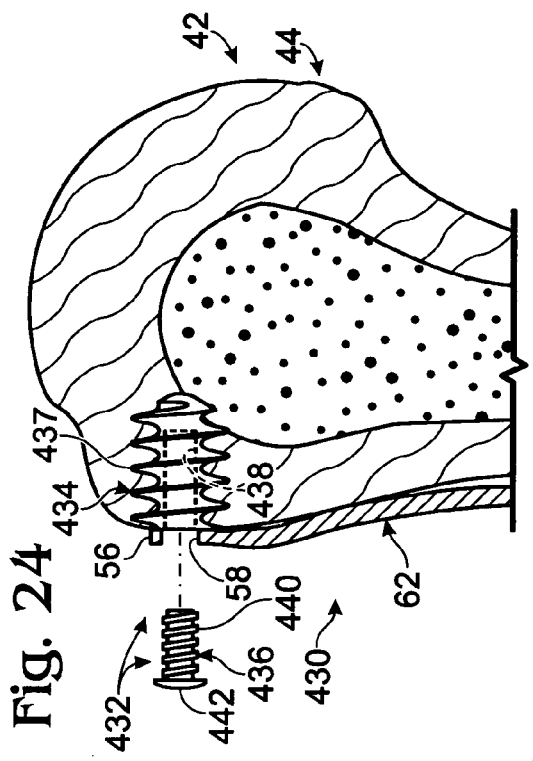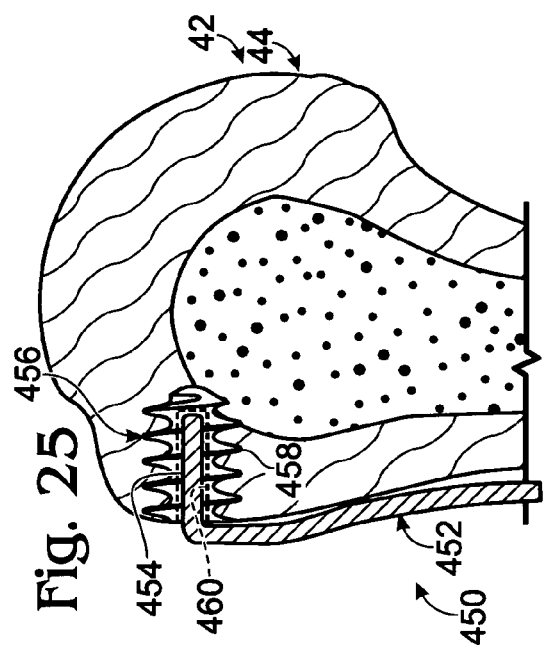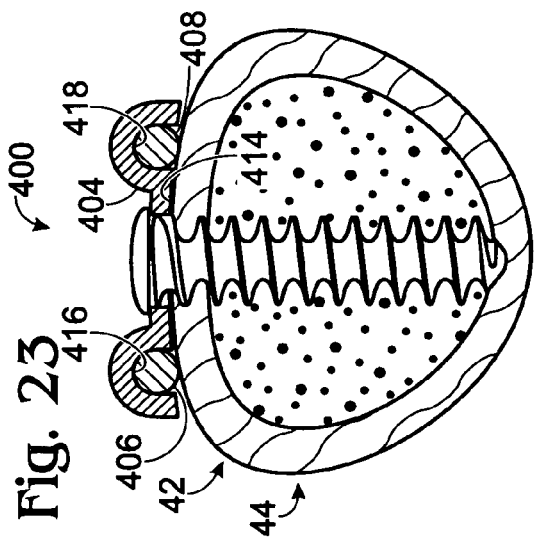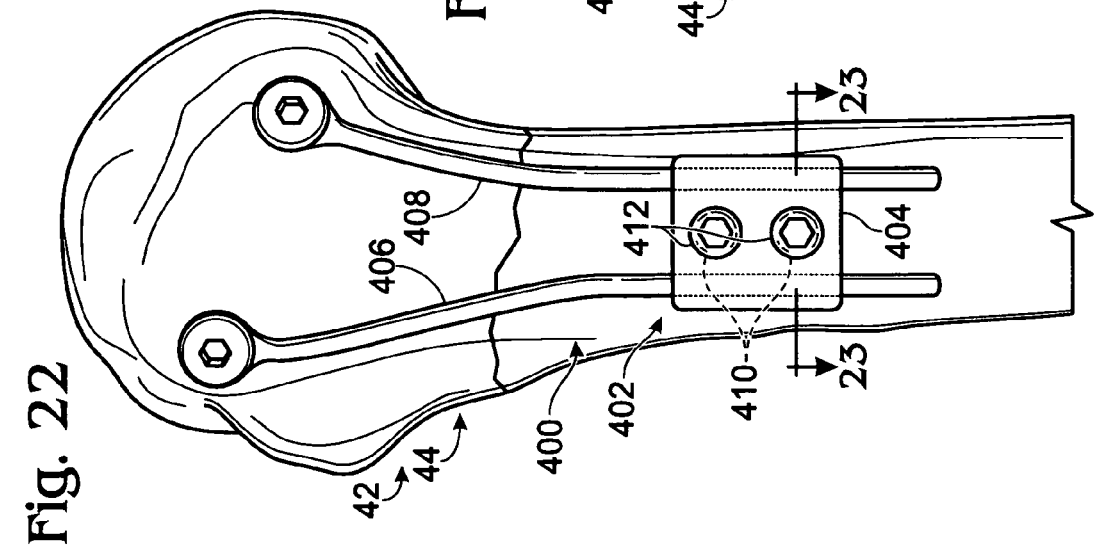

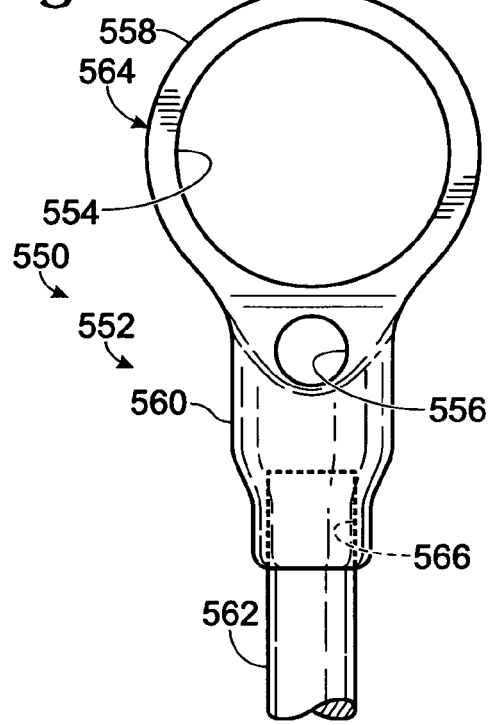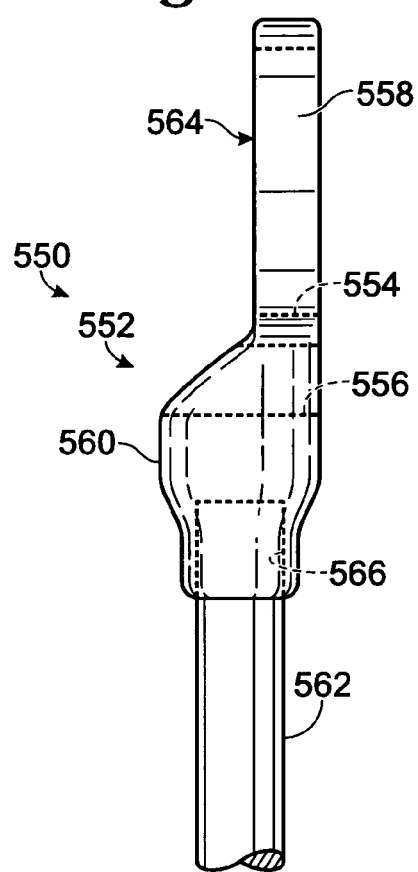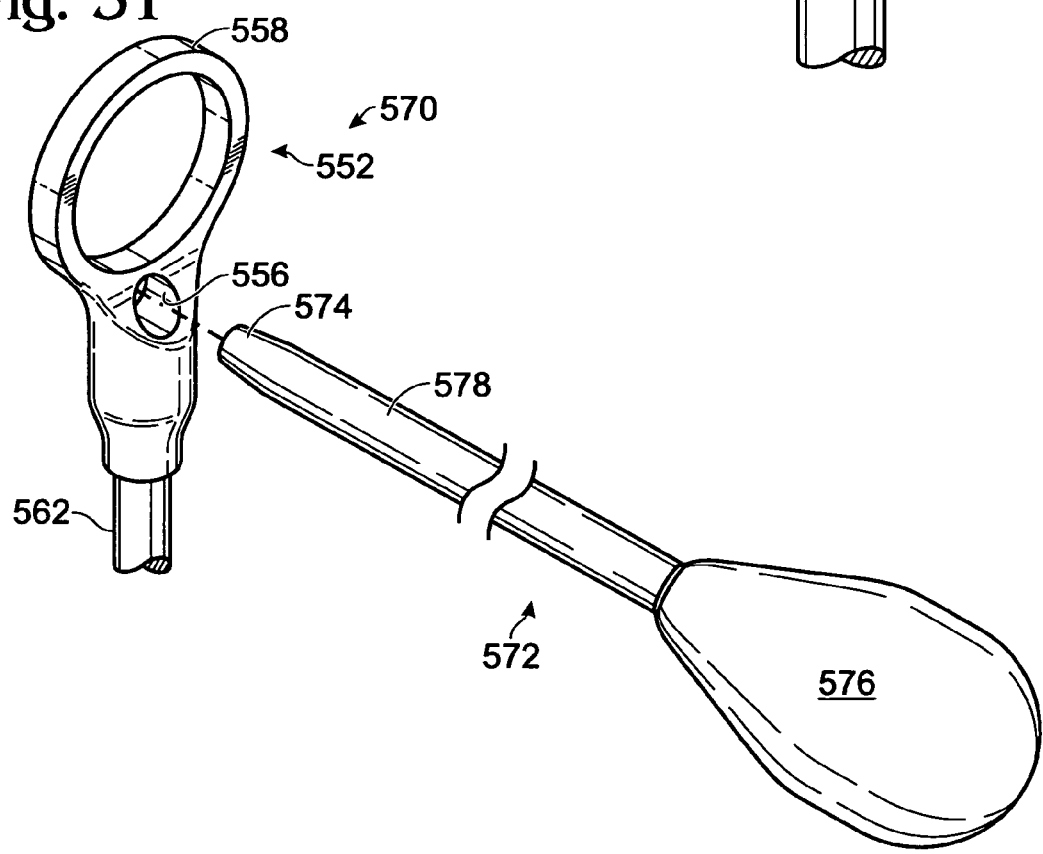

METHOD OF BONE FIXATION WITH SLENDER SPANNING MEMBERS DISPOSED OUTSIDE BONE

CROSS-REFERENCE TO PRIORITY APPLICATION

This application is based upon and claims the benefit under 35 U.S.C. §119(e) of U.S. Provisional Patent Application Ser. No. 60/961,317, filed Jul. 19, 2007, which is incorporated herein by reference in its entirety for all purposes.

BACKGROUND

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using fixation devices that reinforce the fractured bones and keep them aligned during healing. Fixation devices may take a variety of forms, including casts and external fixators for external fixation, and bone plates and/or fasteners (e.g., bone screws) for internal fixation.

Bone plates are implants that may be positioned under skin and other soft tissue for mounting on the bone adjacent the fracture. These plates may be manufactured and/or custom bent for mounting to particular regions of bone. To use a bone plate to repair a fractured bone, a surgeon (1) selects an appropriate plate, (2) reduces (sets) the fracture, and (3) fastens the plate to the bone on opposing sides of the fracture using suitable fasteners, such as bone screws, so that the bone plate spans the fracture and fragments of the bone are substantially fixed in position.

A potential disadvantage to the use of bone plates, particularly in elderly individuals, is the difficulty of fastening the plates to bone near the ends of bones. For example, due to poor bone quality (e.g., osteoporosis or osteopenia) in elderly individuals, bone plates may be fastened to bone via bone screws that are locked to plate apertures, rather than relying solely on threaded engagement with bone to hold each bone screw in position. However, bone plates with locked bone screws may create a very rigid structure that damages bone in response to bone loading, thereby loosening the bone plate.

A distinct approach to fixing fractured bones involves the use of one or more pins to span a fracture. The pins are placed into a fractured bone, with each pin spanning the fracture inside the bone. The use of pins may provide advantages over a plate-based approach to fixation. For example, pins may be more flexible than bone plates. Accordingly, pins tend to permit more micro-motion of otherwise fixed bone fragments, thereby promoting callus formation at the fracture site, which may speed healing and improve the strength of the bone after healing. In addition, pins may be less likely to damage bone than a bone plate fastened with bone screws.

However, the pin-based implants of the prior art may have certain drawbacks. For example, pins inserted into bone may not be anchored adequately to bone and thus may slip, thereby permitting too much movement of bone fragments for proper healing.

SUMMARY

The present disclosure provides a system, including methods, apparatus, kits, and components, for bone fixation using a pair of slender spanning members to span a fracture outside bone.

BRIEF DESCRIPTION OF THE DRAWINGS

FIG. 1 is a view of the proximal portion of a fractured humerus being fixed with an illustrative multi-spanning fixation system including a pair of slender spanning members, in accordance with aspects of the present disclosure.

FIG. 2 is an exploded view of the fractured humerus and multi-spanning fixation system of FIG. 1.

FIG. 3 is a plan view of a base plate from the fixation system of FIG. 1.

FIG. 4 is a fragmentary, plan view of the base plate of FIG. 3 assembled with a cover plate and a spanning element of the multi-spanning fixation system of FIG. 1.

FIG. 5 is a longitudinal sectional view of the base plate, cover plate, and spanning element of FIG. 4, taken generally along line 5-5 of FIG. 4.

FIG. 6 is a transverse sectional view of the base plate, cover plate, and spanning element of FIG. 4, taken generally along line 6-6 of FIG. 4.

FIG. 15 is a view of a proximal portion of a fractured left humerus with another illustrative multi-spanning fixation device partially installed on the humerus and with a wire of the fixation device in a slidable configuration, in accordance with aspects of the present disclosure.

FIG. 16 is a view of a proximal portion of a fractured left humerus with the fixation device of FIG. 15 partially installed on the humerus and with the wire being urged distally such that the wire moves in relation to a plate assembly of the fixation device, to compress the humerus longitudinally, in accordance with aspects of the present disclosure.

FIG. 17 is a view of a proximal portion of a fractured left humerus with the fixation device of FIG. 15 fully installed, in accordance with aspects of present disclosure.

FIG. 18 is a sectional view of the fixation device of FIG. 17, taken generally along line 18-18 of FIG. 17.

FIG. 19 is a plan view of selected portions of the humerus and fixation device of FIG. 17 after installation of a spacer to hold the wire in place, in accordance with aspects of the present disclosure.

FIG. 20 is a view of a proximal portion of a fractured left humerus being fixed with yet another illustrative multi-spanning fixation system, with a fixation device of the system including a cover plate that covers at least most of a base plate of the fixation device, in accordance with aspects of present disclosure.

FIG. 21 is a sectional view of the fixation system of FIG. 20, taken generally along line 21-21 of FIG. 20 in the absence of bone.

FIG. 22 is a view of a proximal portion of a fractured left humerus being fixed with still another illustrative multi-spanning fixation system, with a fixation device of the system including a plate that holds wires against bone, in accordance with aspects of the present disclosure.

FIG. 23 is a sectional view of the humerus and multi-spanning fixation system of FIG. 22, taken generally along line 23-23 of FIG. 22.

FIG. 24 is a fragmentary, longitudinal sectional view of a left humerus being fixed with still yet another illustrative multi-spanning fixation system, with the system including a threaded assembly for securing a wire of the system to bone, in accordance with aspects of the present disclosure.

FIG. 25 is a fragmentary, longitudinal sectional view of a left humerus being fixed with another illustrative multi-spanning fixation system, with the system including a wire that extends into bone, in accordance with aspects of present disclosure.

FIG. 29 is a fragmentary elevation view of an exemplary fixation device including a spanning member with an auxiliary opening defined near an end of the spanning member, in accordance with aspects of the present disclosure.

FIG. 30 is a fragmentary side view of the fixation device of FIG. 29.

FIG. 31 is an exploded view of an assembly including the spanning member of FIG. 29 and an exemplary tool configured to be coupled with the spanning member via the auxiliary opening, to permit the position of a head of the spanning member to be adjusted using the tool to twist and/or bend a wire body portion of the spanning member, in accordance with aspects of present disclosure.

DETAILED DESCRIPTION

Figure 7:
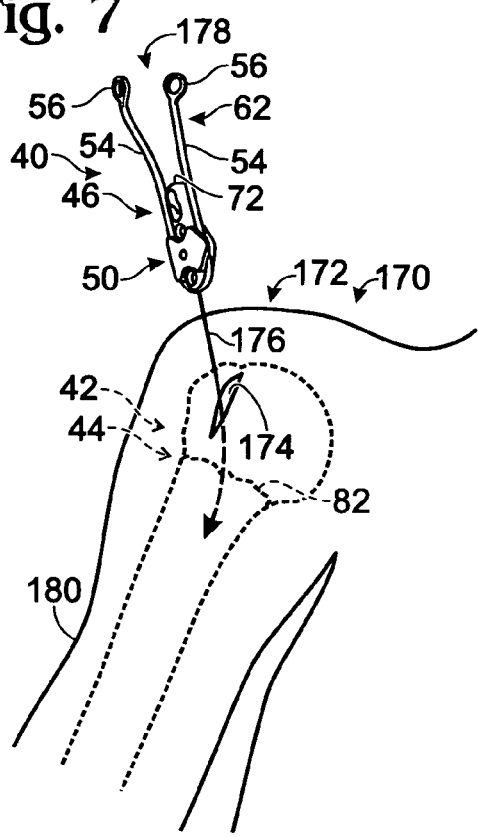
FIG. 7 is a fragmentary view of the shoulder region of an implant recipient with a fractured proximal humerus during performance of an illustrative method of fixing a bone using the multi-spanning fixation system of FIG. 1, with a fixation device of the system being placed on the humerus through a first incision, in accordance with aspects of the present disclosure.

The present disclosure provides a system, including methods, apparatus, kits, and components, for bone fixation using a pair of slender spanning members to span a fracture outside bone. The system may include and/or use a multi-spanning fixation device that spans a bone discontinuity, such as a fracture or cut, at least twice. The fixation device may include a plate member, also termed a retainer, defining one or more apertures and also may include a pair of slender spanning members connected to the plate member. The spanning members may be disposed laterally of one another and may extend in the same general direction from the plate member (i.e., collectively forming an angle of ninety degrees or less). Each spanning member may include a wire body portion extending from the plate member to a respective head. The head may be formed at an end of the wire body portion opposite the plate member and may define an opening. The heads of the spanning members may be separate from one another. For example, the spanning members may be connected to one another in the fixation device only generally opposite the heads along the spanning members, thereby permitting adjustment of a relative spacing and/or angulation of the heads by deformation of at least one of the wire body portions. The plate member and the heads of the spanning members may be configured to be disposed on respective opposing sides of a fracture in a bone, such as near the proximal end of a humeral bone, with each wire body portion spanning the fracture outside the bone and attached to the bone using fasteners received in at least one aperture of the plate member and in the respective openings of the heads of the spanning members.

The fixation devices disclosed herein, and their methods of use, may solve a number of problems that may be encountered during fixation with pins or bone plates. For example, the fixation devices may provide better attachment to bone than pins placed into bone and thus more stable bone fixation (and less chance of implant migration, which may result in tissue irritation or injury). In addition, the fixation devices may permit more micro-motion at a fracture site than a bone plate, to provide better callus formation and to place less stress on bone around fasteners. Accordingly, a fixation device according to present disclosure may permit bone to heal more quickly and effectively than the use of pins or a bone plate.

The following sections describe further aspects of the present disclosure, including, among others, (I) an illustrative multi-spanning fixation system, (II) an illustrative method of installing a multi-spanning fixation system, (III) an illustrative insertion tool a multi-spanning fixation device, (IV) spanning elements, (V) plate members, (VI) fasteners, (VII) composition of system components, (VIII) methods of fixing bones, (IX) kits for fixing bones, and (X) examples.

I. Illustrative Multi-Spanning Fixation System

FIGS. 1 and 2 show respective assembled and exploded views of an illustrative multi-spanning fixation system 40 installed on (FIG. 1) and exploded from (FIG. 2) an exemplary bone 42, namely, left humerus 44. System 40 may include a fixation device 46, also termed a wire-plate device, disposed on bone 42 and secured to the bone with a plurality of fasteners 48 (see FIG. 2) received in openings/apertures of the fixation device. The terms "opening" and "aperture," as used herein, have the same meaning. Both terms are used to improve clarity.

Fixation device 46 may include a plate member 50 and at least or only a pair of slender spanning members 52. The spanning members may be connected to the plate member, for example, secured to the plate member. Accordingly, the plate member and the spanning members may be discrete pieces (e.g., provided by two-piece (or more) construction) or may be connected integrally as one piece (e.g., as a monolith).

Each spanning member may include a wire body portion 54. The wire body portion, which is a slender bar or rod and which may be termed a shaft, may extend from the plate member to span a bone discontinuity, such as a fracture, outside bone. The spanning members (and wire body portions/shafts) may be rigid enough to hold bone fragments in position (i.e., fix the bone) as the fractured bone heals, but flexible enough to permit micro-motion that promotes healing and that resists damage to the bone by the fasteners upon bone loading. Accordingly, in some embodiments, the wire body portion may have a width of at least 1.5 millimeters or at least 2 millimeters and may have a flexibility more comparable to a Steinmann pin than a K-wire. The wire body portion may be round or generally rectangular in cross section, among others. The term "wire," as used herein, describes a structure that is long and slender, with a width and a thickness that are about the same (i.e., less than two-fold different) and much less (e.g., at least about 10- or 20-fold less) than the length.

Each spanning member also may include a head 56 formed at an end of the wire body portion. The head and the wire body portion of the spanning member may be formed by the same monolithic structure or may be formed by discrete pieces that are attached to one another, e.g., fixedly or pivotably, among others. Head 56 is wider than wire body portion 54 and defines at least one opening 58 configured to receive a fastener, such as a threaded fastener (e.g., a bone screw), that secures head 56 to bone. The opening may have a continuous (i.e., closed) perimeter and/or a seamless perimeter. In other words, the opening may be bounded circumferentially to form a closed loop. In some embodiments, the head may have the same or a different thickness than the wire body portion, e.g., being thinner than the wire body portion. Alternatively, or in addition, a wall 60 (see FIG. 2) extending at least mostly or completely around opening 58 may have the same or a different width than the wire body portion, e.g., being wider or narrower than the wire body portion.

The heads may be separate from one another near the ends of the wire body portion. Accordingly, the spanning members may extend from the plate member as separate structures that are connected to one another in the fixation device only generally opposite the heads (e.g., connected to one another in the fixation device only via the wire body portions and/or plate member). With this arrangement, the spanning members and particularly the heads may be moved relative to one another, such as by deforming one or more of the wire body portions, to provide a more customized fit to bone by adjusting the relative spacing and/or angulation of the heads.

The spanning members may be provided by one or more spanning elements that are discrete from plate member 50. A spanning element may be generally linear or may bend by less than ninety degrees, or may bend even more substantially, such as approximately 180 degrees, to form wire body portions 54, also termed fingers or legs, disposed laterally from one another and extending to heads 56. For example, the spanning members may be provided by a generally U-shaped wire 62, among others. FIG. 2 shows U-shaped wire 62 including an arcuate base region 64 extending to wire segments 66, which form laterally disposed wire body portions 54 that extend to heads 56.

Each spanning member (and/or wire body portion/shaft and/or wire segment) may be nonlinear, with a bent configuration corresponding to a surface contour near an end of a bone. In some examples, the spanning member may be pre-bent, meaning that a bent configuration is introduced pre-operatively, such as during manufacture of the fixation device. The bent configuration may be imposed or created from a precursor structure by any suitable procedure, including deforming, cutting, or milling, among others. A spanning member thus may be configured to extend along an exterior surface region 70 of the bone, such as near an end of the bone. Each spanning member, and particularly a wire body portion/shaft or wire segment thereof, may extend nonlinearly according to a nonlinear contour and/or profile of exterior surface region 70, such that at least a region of the spanning member (e.g., at least a portion of each wire body portion) has a shape (and/or a bent configuration and/or an inner surface) that generally matches the contour and/or profile of the exterior surface region of the bone, to maintain a low profile of the spanning member above the bone. The spanning member may be disposed at least mostly (or completely) adjacent the exterior surface region of the bone, that is, on and/or in close proximity to the exterior surface region and at least mostly or completely outside the bone. Whether and where the spanning member is in contact with the bone surface, or is held in a slightly spaced position above the bone surface, may be determined by the shape of the spanning member and/or by the structure of fasteners 48 and/or plate member 50, among others.

Fixation device 46 may use plate member 50 as an anchor portion or retainer that attaches the spanning members to bone on one side of a bone discontinuity via one or more fasteners 48. Alternatively, the spanning members and/or a spanning element may be secured to bone only with fasteners 48 and thus may be used without a plate member. In some embodiments, the fixation device may be an assembly of one or more spanning members and a plate member that are discrete pieces and that can be connected to each other separately from bone, to form a unit. Accordingly, the fixation device may be placed on bone and/or attached to bone as a pre-assembled unit of two or more pieces or as a one-piece construct, or may be assembled on bone.

Plate member 50 may include one or more plate-shaped components defining one or more apertures for receiving fasteners 48 that secure the plate-shaped components to each other, to one or more spanning elements, to bone, or any combination thereof. For example, here, plate member 50 includes a base plate 72 (an inner plate) and a cover plate 74 (an outer plate) that fastens to the base plate via a cover fastener 76 (FIG. 2). A spanning element, such as wire 62, may extend between the base plate and the cover plate such that at least a portion of the spanning element is held in a spaced relation to bone and such that movement of the spanning element is restricted. In particular, one or more regions of the spanning element may be received in a channel 78 defined by the base plate, the cover plate, or both (FIG. 1). Here, channel 78 is divided into three parts and is generally U-shaped.

The bone may include only one or at least one discontinuity 80, such as a fracture 82 (FIG. 1). Here, fracture 82 is the only substantial discontinuity in bone 42 and extends transversely through the bone, near a head 84 of the bone, to divide the bone into exactly two fragments: a shorter proximal fragment 86 and a longer distal fragment 88. The fixation device disclosed herein may be most suitable for fixation of a bone fractured into two parts (i.e., with only one fracture). However, in other examples, bone 42 may have multiple discontinuities, such as multiple fractures, and may be divided into two or more fragments of equal or unequal length/size. If of unequal length/size, a shorter/smaller fragment may be disposed proximally or distally. In any event, spanning members 52 may span discontinuity 80 at least or exactly a pair of times outside of bone 42, transversely to the discontinuity, and, optionally, generally parallel to the long axis of the bone.

FIG. 3 shows a plan view of base plate 72. The base plate may define a plurality of apertures 90-96 for receiving fasteners, each of which may or may not extend into bone. For example, apertures 90-94 may be structured to receive respective bone screws 98-102 (see FIG. 2) that extend through the apertures and into bone 42.

The apertures may be shaped according to the angle at which the bone screws may be directed into bone. For example, apertures 92 and 94 may be circular to direct bone screws 100 and 102 in a substantially or relatively more perpendicular direction through the base plate and into bone. Aperture 90 may be elongate to permit bone screw 98 to be directed obliquely into bone.

In any event, apertures 90-94 may include respective countersinks 104-108 for at least partially receiving heads of the bone screws (and/or other fasteners). The countersinks may be disposed symmetrically or asymmetrically with respect to the apertures. For example, countersink 104 may be disposed asymmetrically along aperture 90, to guide and/or accommodate hole formation and/or fastener placement obliquely with respect to a plane defined by the base plate. Accordingly, bone screw 98 may be longer than bone screws 100 and 102 to allow obliquely oriented bone screw 98 to span a discontinuity in the bone.

In some embodiments, another bone screw 110 (shown in FIG. 2 in phantom outline for clarity) may be used in place of bone screw 98. Bone screw 110 may have a partially nonthreaded shaft 112, to provide a smooth or nonthreaded tip 114. Bone screw 110 thus may extend into a pair of fragments (e.g., fragments 86 and 88 of FIG. 1) but may be disposed in threaded engagement with only one fragment of the pair (e.g., distal fragment 88 (the fragment on the near side of the discontinuity)). The use of a partially nonthreaded bone screw may allow slight movement of the bone fragments, to promote callus formation and healing.

Base plate 72 may define, at least partially, a channel for receiving one or more segments of wire 62. For example, here, base plate 72 defines a pair of longitudinal grooves 116 disposed bilaterally from the midline of the plate and formed in an outer face 118 of the base plate. The longitudinal grooves may extend substantially longitudinally with respect to the base plate and/or with respect to a bone on which the base plate is installed (i.e., generally parallel to the long axis of the base plate and/or bone). The longitudinal grooves may extend linearly, as shown here, or nonlinearly, and the base plate may have one, two, or more longitudinal grooves. In some embodiments, the base plate may be wider where the longitudinal grooves are formed. For example, here, base plate 72 has wings 120 that form a head 122 of the base plate. The wings and/or the head of the base plate may have any suitable shape, such as generally circular, elliptical, and/or the rounded polygon shown here, among others. Alternatively, or in addition, base plate 72 may define at least one transverse groove 124, which may be formed in any suitable surface of the base plate, such as an end surface 126 (and/or a side surface) of the base plate. The transverse groove may have a shape that matches a bent region of the wire, for example, a curved transverse groove that matches a curved region of the wire.

FIG. 4 shows selected portions of fixation device 46 in a pre-assembled configuration. In particular, wire 62 may be received in channel 78 formed collectively by base plate 72 and cover plate 74 of plate member 50. End regions of wire segments 66 may be received in corresponding channel portions 127, 128 formed at least in part by longitudinal grooves 116 of the base plate (see FIGS. 3 and 4). Bent base region 64 of wire 62 may be received at least partially in transverse groove 124 of base plate 72, such that the wire extends or wraps generally around an end region of the base plate.

Cover plate 74 may be disposed over the base plate to cover at least a portion of the base plate and the wire. For example, cover plate 74 may extend laterally over a region of each segment 66 of the wire and over at least a portion of wings 120 and head 122 of the base plate (see FIGS. 3 and 4). Cover plate 74 also may extend longitudinally to cover any suitable portion of the base plate. Here, the cover plate does not extend over any of apertures 90-94, but in other embodiments the cover plate may extend over one or more (or all) of the apertures used to secure the base plate to bone (e.g., see Section X, Example 2).

FIG. 5 shows a longitudinal sectional view of fixation device 46. Cover plate 74 may be attached to base plate 72 via cover fastener 76 received in an aperture 130 of the cover plate. The cover fastener may extend through aperture 130 for threaded engagement with locking aperture 96 of base plate 72 (e.g., via an internal thread 132 of aperture 96). In some embodiments, aperture 96 of the base plate may be nonlocking such that cover plate 74 may be secured by a fastener that extends through aperture 96 and into threaded engagement with underlying bone. Aperture 130 may include a countersink 134 for receiving at least a portion of a head 136 of cover fastener 76.

Wire 62 may be held in a spaced relation to bone, for at least a portion of the wire, such as end region of the wire that overlaps plate member 50. In particular, channel 78 may be disposed above and in a spaced relation to an inner face 138 of the base plate that faces bone. Channel 78 also may be disposed below outer face 118 of the base plate 72 and/or plate member 50, in a spaced relation to the outer face. Channel 78 may have a substantially planar configuration, as shown here, to receive a substantially planar portion of wire 62 provided by end region thereof, or channel 78 and/or the end region may be nonplanar.

FIG. 6 shows a transverse sectional view of fixation device 46. The base plate and cover plate may have any suitable surface contours. For example, at least a portion of channel 78 may be formed cooperatively by base plate 72 and cover plate 74. Cover plate 74 may define longitudinal grooves 140 using an inner surface 142 of the cover plate. Grooves 140 may align with grooves 116 of the base plate to form segments of channel 78. In addition, inner surface 142 of the cover plate may have a complementary shape to the outer face of base plate 72. For example, base plate 72 may form a longitudinal ridge 144 that fits together with a corresponding furrow 146 of cover plate 74. Furthermore, the outer and inner faces of the base plate may match or be non-matching. For example, inner face 138 may have a concave surface region 148 for engagement with a corresponding convex surface region of bone.

II. Illustrative Method of Installing a Multi-Spanning Fixation System

FIGS. 7-10 show configurations produced during performance of an illustrative method of fixing a bone using multi-spanning fixation system 40 (e.g., see FIGS. 1-6). The method is shown being performed on an implant recipient 170, with only a left shoulder region 172 of the plate recipient visible in these figures. The left shoulder region is being viewed generally from the side and back of the implant recipient, with the presentation schematized somewhat for simplicity and clarity.

FIG. 7 shows wire-plate device 46 of system 40 being placed on bone 42 (humerus 44) through a first incision 174 over the humerus. Incision 174 may be formed on the lateral side of the humerus, near the proximal end of the bone. The incision may be formed centrally over the humerus with respect to the anterior-posterior axis of the recipient's body, or more toward the anterior aspect or the posterior aspect of the humerus. Incision 174 may be substantially shorter than the length of fixation device 46 and may be created in a nonoverlapping relationship with fracture 82 and/or with a target site for plate member 50 of fixation device 46.

Fixation device 46 may be placed through incision 174 and onto humerus 44, as indicated by motion arrow 176. Placement of the fixation device may involve advancing the device as a pre-assembled unit 178 through the incision and along an exterior surface region of bone, under soft tissue/skin 180. Alternatively, wire 62 and plate member 50 may be placed on and/or adjacent bone separately for assembly on bone, such as with the wire being disposed on/adjacent bone before or after base plate 72. In any event, device 46 may be placed such that plate member 50 and wire body portions 54 of wire 50 are disposed more centrally on humerus 44 (or another bone 42) relative to heads 56 of wire 62. Accordingly, plate member 50 and wire body portions 54 of wire 62 may be placed through the incision before heads 56 and advanced distally from the incision, for a fracture of the proximal humerus. Fixation device 46 may be grasped by hand during placement through the incision or may be manipulated by a distinct tool(s). An illustrative holder/insertion tool that may be suitable is described below in Section III.

Figure 8:
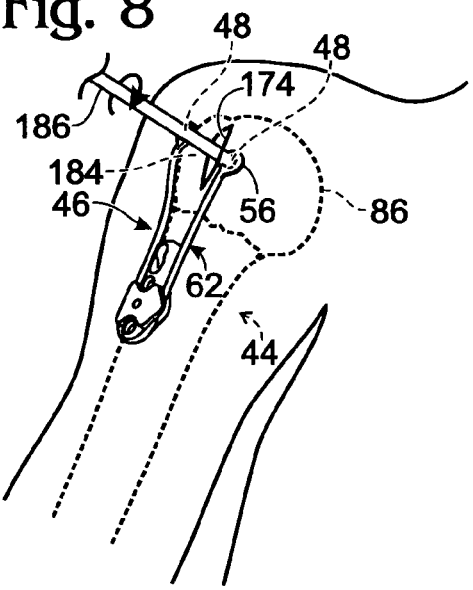
FIG. 8 is a fragmentary view of the shoulder region of the implant recipient of FIG. 7 during performance of an illustrative method of fixing a bone using the multi-spanning fixation system of FIG. 1, with the fixation device of FIG. 7 disposed on the humerus and being secured to a proximal fragment of the humerus with fasteners received in openings defined by the slender spanning members of the fixation device, in accordance with aspects of the present disclosure.
Figure 9:
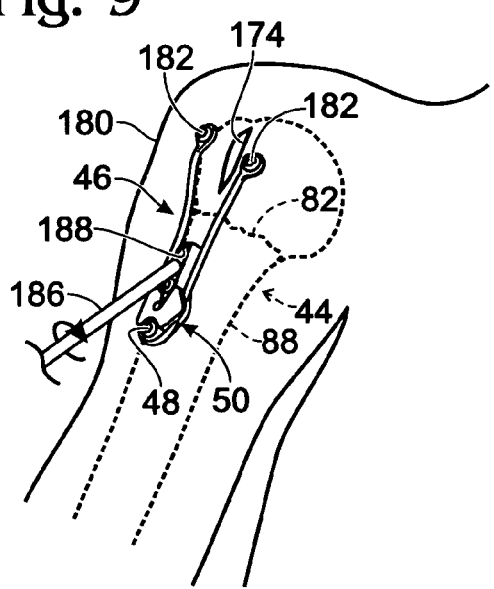
FIG. 9 is a fragmentary view of the shoulder region of the implant recipient of FIG. 7 during performance of an illustrative method of fixing a bone using the multi-spanning fixation system of FIG. 1, with the fixation device of FIG. 7 being secured to a more distal fragment of the humerus using fasteners received through a second incision and through apertures defined by the base plate of the fixation device, in accordance with aspects of the present disclosure.

FIG. 8 shows fixation device 46 disposed on humerus 44 and being secured to proximal fragment 86 of the humerus with fasteners 48, such as cancellous bone screws 182 (also see FIGS. 2 and 9). Wire-plate device 46 may be disposed such that heads 56 and/or openings 58 of wire 62 are positioned adjacent proximal fragment 86, for example, near and/or against greater tuberosity 184. The cancellous bone screws or other suitable fasteners 48 may be placed through wire openings and threaded into proximal fragment 86 using a driver 186 received through incision 174. The fasteners may engage bone or another fastener pre-installed in proximal fragment 86 (e.g., see Section X, Example 4). Furthermore, each fastener 48 may urge wire 62 against bone and/or against another pre-installed fastener and/or may lock to a head of wire 62 via an internal thread formed in an opening of the wire's head.

FIG. 9 shows wire-plate device 46 being secured to distal fragment 88 of humerus 44. A second incision 188 (or a plurality of small incisions disposed over and aligned with the apertures of the base plate) may be formed through soft tissue 180 over plate member 50. The second incision may be generally aligned longitudinally with first incision 174 and may be spaced from the first incision, to provide a less-invasive approach to installing wire-plate device 46. Alternatively, a single longer incision may be created for installing the wire-plate device and all fasteners through openings/apertures of wire-plate device 46. In any event, fasteners 48 (e.g., bone screws 98-102 of FIG. 2) may be placed through openings 90-94 of base plate 72 (see FIG. 3) and into distal fragment 88 of humerus 44, using driver 186 (or a distinct driver). One or more of the fasteners may be placed at an oblique angle to extend across fracture 82.

Figure 10:
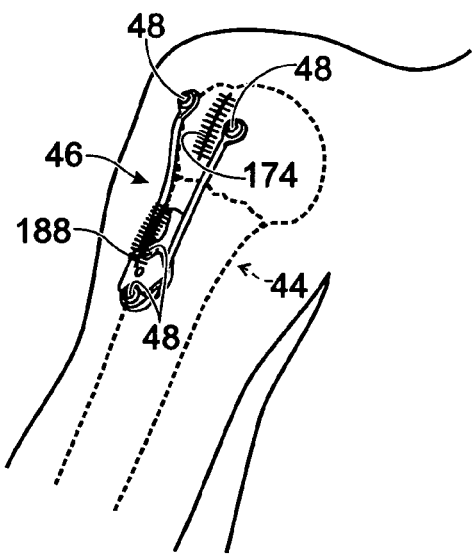
FIG. 10 is a fragmentary view of the shoulder region of the implant recipient of FIG. 7 during performance of an illustrative method of fixing a bone using the multi-spanning fixation system of FIG. 1, with the fixation device of FIG. 7 fully secured to the humerus and with both incisions closed, in accordance with aspects of the present disclosure.

FIG. 10 shows wire-plate device 46 fully secured to humerus 44 with fasteners 48. Both incisions 174, 188 may be closed, such as with sutures, staples, or cement, among others. Device 46 may be removed after humerus 44 has healed sufficiently or may be left in place indefinitely.

III. Illustrative Insertion Tool for a Multi-spanning Fixation Device

FIGS. 11-14 show the structure and use of an illustrative insertion tool 200 that may be included in multi-spanning system 40. Tool 200 also may be described as and/or may include (1) a holder for an orthopedic implant (e.g., for a bone plate, a retainer, a wire, and/or a wire-plate assembly, among others), (2) a guide device for guiding formation of holes through opening/apertures of an orthopedic implant, and/or (3) a path-forming device that leads an orthopedic implant along bone and under soft tissue by creating a path under the soft tissue for travel of the orthopedic implant. Although illustrated with wire-plate device 46, tool 200 may be suitable for placement of a bone plate that is being used without a wire and thus the term orthopedic implant in this section is intended to encompass a bone plate alone. Furthermore, tool 200 may be suitable for placement of a wire that is used without a plate member.

Figure 11:
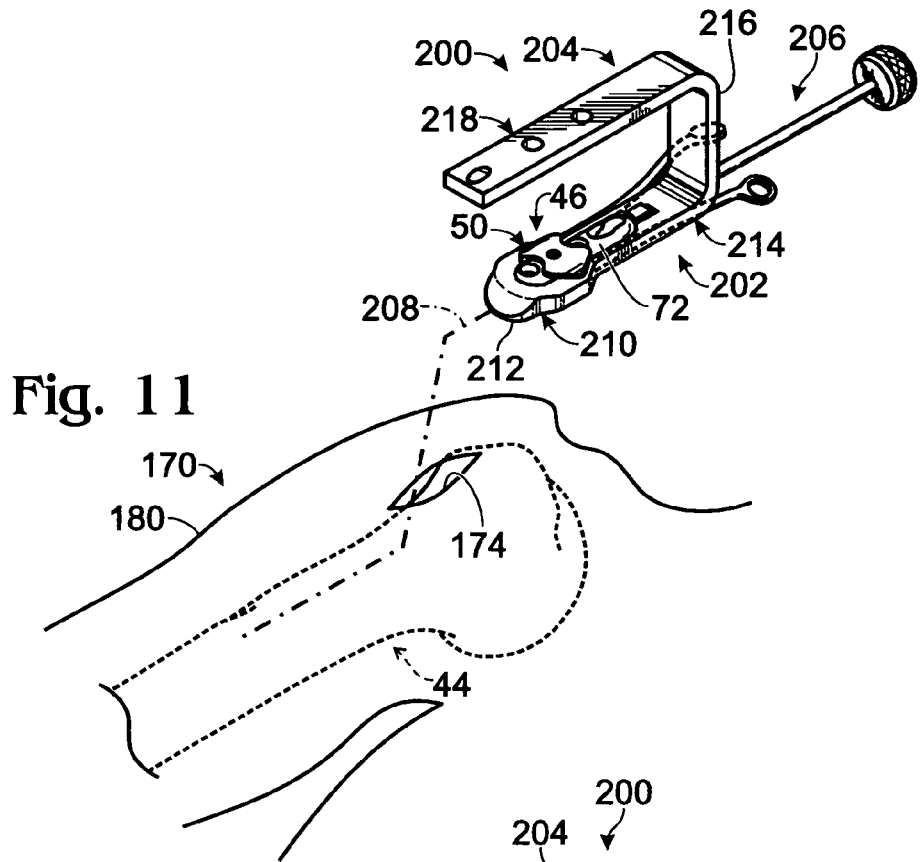
FIG. 11 is a fragmentary view of the shoulder region of an implant recipient during placement of the fixation device of FIG. 7 on the humerus using an illustrative insertion tool that may be included in the fixation system, in accordance with aspects of the present disclosure.
Figure 12:
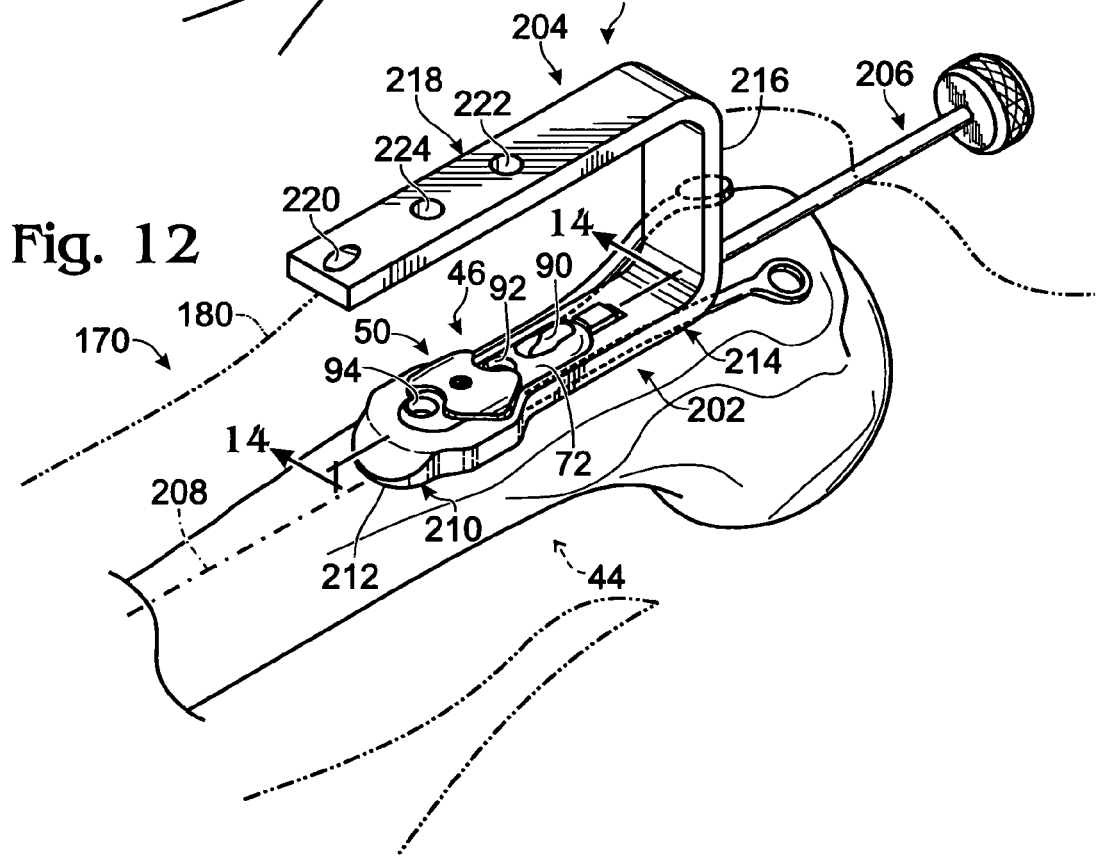
FIG. 12 is a fragmentary view of the shoulder region of an implant recipient after placement of the fixation device of FIG. 7 on the humerus using the insertion tool of FIG. 11, and before removal of the insertion tool, in accordance with aspects of the present disclosure.

FIGS. 11 and 12 show wire-plate device 46 attached to insertion tool 200 respectively before and after the device is placed on humerus 44 through first incision 174 using the insertion tool. The insertion tool may include an internal portion 202, an external portion 204, and a releasable coupling mechanism 206 (also termed a detent mechanism).

Internal portion 202 may be structured to be disposed temporarily inside the body of implant recipient 170. The internal portion may be configured to engage device 46 and to carry at least a portion of device 46 through incision 174 and under soft tissue 180 of the implant recipient. The internal portion thus may have a relatively low profile and may be sized and shaped to minimize undesired damage to surrounding soft tissue. For example, the internal portion may have smooth contours and rounded edges to minimize undesired damage to the soft tissue. In addition, internal portion 202 and the orthopedic implant may have long axes that are substantially aligned. Internal portion 202 and a coupled orthopedic implant thus may have a collective thickness that is no more than about 50% greater than the thickness of the implant alone. Alternatively, or in addition, the internal portion may have a thickness that is about the same as or less than the thickness of the orthopedic implant (and/or a plate member thereof). Moreover, the internal portion coupled to the orthopedic implant may have a collective width that is no more than about 50% greater than the width of the orthopedic implant (and/or a plate member thereof). Alternatively, or in addition, the internal portion may have a width that is not much greater than the width of the orthopedic implant (and/or a plate member thereof), such as less than about 50%, 25% or 10% greater than the width of the implant/plate member. In some embodiments, the width of the internal portion may be about the same as or less than the width of the implant and/or a plate member thereof.

The length of internal portion 202 may be greater than the length of the orthopedic implant (and/or a plate member thereof) to which the internal portion is coupled. In particular, internal portion 202 (and/or the implant/plate member) may define a long axis 208 and the internal portion may extend along the long axis to a position forward of a leading end of the orthopedic implant (and/or a plate member thereof) to form a leading region 210. The leading region may travel in front of the leading end of the implant/plate member to create a path for the implant/plate member. Leading region 210 thus may have a structure that effects or promotes separation of soft tissue from bone. For example, leading region 210 may taper away from the implant/retainer to form a blade structure 212. The blade structure may be sharper than the leading end of the implant/plate member. Internal portion 202 also may have a trailing region 214 disposed rearward of a trailing end of the implant/plate member along long axis 208. Trailing region 214 may have a length that is at least as great as the distance that the trailing end of the implant/plate member is to be advanced under soft tissue (e.g., from incision 174).

External portion 204 may be configured to be disposed outside of the implant recipient during installation of the implant/plate member. The external portion thus may include a bridge region 216 that extends from trailing region 214 of internal portion 202. Bridge region 216 may connect the internal and external portions of tool 200 and may at least partially define the relative dispositions of the internal and external portions. In addition, the external portion may include a guide region 218 for guiding a hole forming tool (i.e., a drill), a driver, and/or a fastener. The guide region may extend in substantially the same direction as internal portion 202 such that the guide region is outwardly spaced from, overlying, and, optionally, substantially parallel to the internal portion (e.g., disposed orthogonally outward of a plane defined by the internal portion). The guide region (and/or guide elements coupled to the guide region) may define guide paths for forming holes and/or placing fasteners through apertures/openings of the implant/plate member. For example, the guide region may include one or more openings 220-224 that are aligned with respective apertures 90-94 of base plate 72 (see FIG. 12). The external portion (e.g., bridge region 216 and/or guide region 218) also may function as a handle, such that the tool can be grasped and manipulated by hand.

Figure 13:
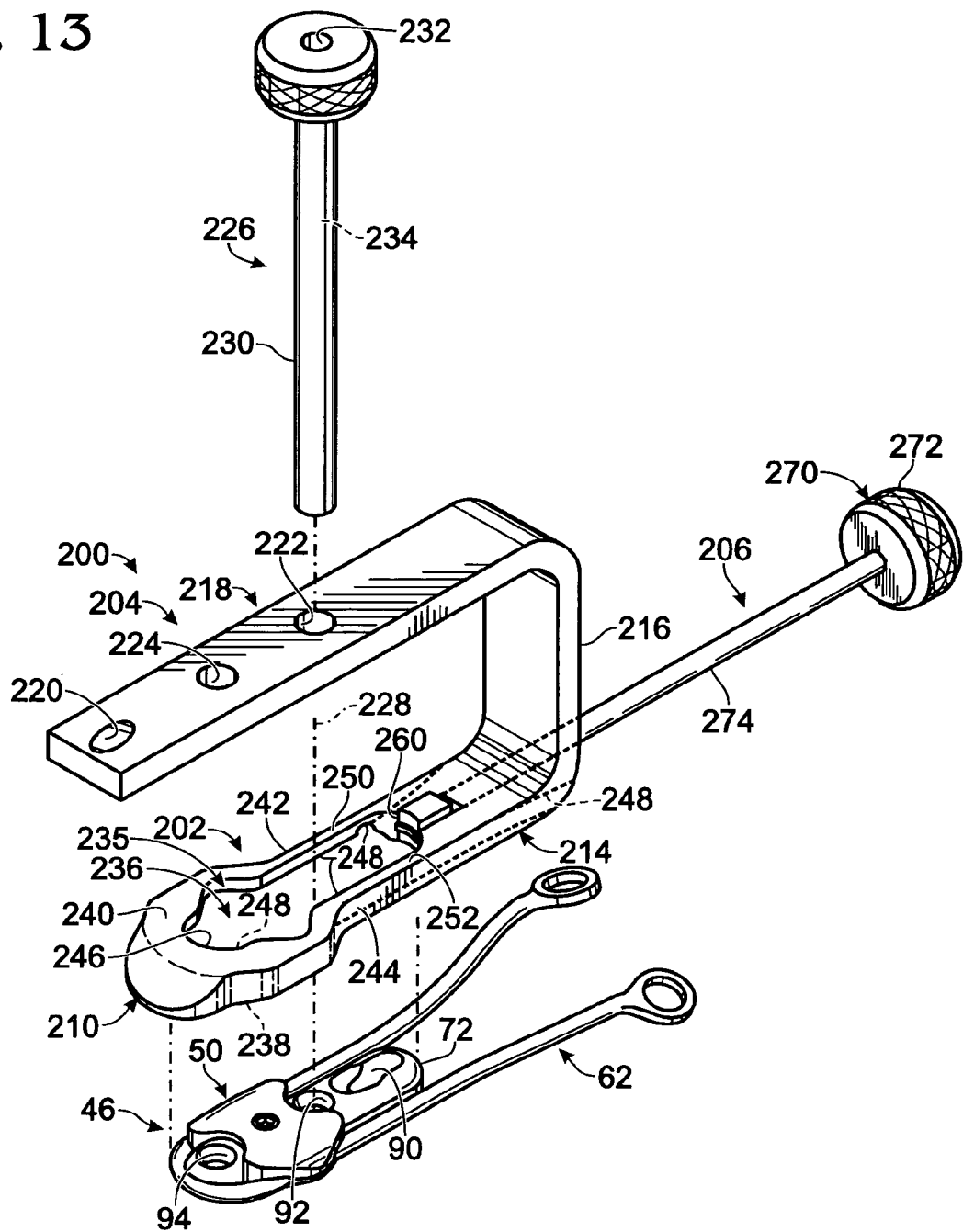
FIG. 13 is an exploded view of the insertion tool and fixation device of FIG. 11, including a guide element that may be included in the insertion tool to guide hole formation and/or fastener placement, in accordance with aspects of the present disclosure.

FIG. 13 shows an exploded view of insertion tool 200 and wire-plate device 46. Insertion tool 200 may include at least one guide element 226 that is coupled or couplable to guide region 218 of external portion 204. The guide element may be structured to be received in one or more of openings 220-224, and in turn may receive and guide translational movement of a hole-forming tool (a drill), a fastener, and/or a driver along a guide path to an opening/aperture of the implant/plate member. For example, here, guide element 226 defines a guide path 228 extending through aperture 92 of base plate 72. The guide element may be attached removably or substantially nonremovably to guide region 218, or may be integral to the guide region. If attached removably, the guide element may be slidable into and out of each opening (220-224) of guide region 218. For example, guide element 226 may be removed from opening 222 and placed into oblique opening 220 to define an oblique guide path extending through oblique aperture 90 of base plate 72. In some embodiments, insertion tool 200 may be provided with a distinct guide element 226 for each opening 220-224 of guide region 218.

The guide element may have any suitable structure. For example, the guide element may include a hollow cylinder or a tube 230 (which may be or include a cannula) that defines an elongate passage 232 for receiving a drill bit, a fastener, and/or a driver tip, among others. The guide element may include indicia 234 arranged along the guide element, and visible from outside the guide element, to facilitate measuring the translational position of the guide element with respect to external portion 204.

Insertion tool 200 may be structured to receive an implant/plate member. In particular, the insertion tool may include a receiver structure 235 for engagement of the implant/plate member. Receiver structure 235 may hold the implant/plate member in a substantially fixed configuration with respect to the internal portion (and/or insertion tool). Leading region 210 and trailing region 214 of internal portion 202 may opposingly flank receiver structure 235. The receiver structure may, for example, include a cavity 236 defined, at least in part, by internal portion 202 for receiving the implant/plate member.

The cavity may have any suitable shape. For example, the cavity may be shaped for receiving the implant/plate member from below (and toward) an inner face (bone facing surface) 238, from above (and toward) an outer face (bone opposing surface) 240, and/or from one or both sides/edges 242, 244 of internal portion 202. Here, cavity 236 is shaped to receive wire-plate device 46 from inner face 238, that is, from below internal portion 202 if tool 200 is oriented as shown in FIG. 13. The cavity may be shaped in correspondence with the orthopedic implant/plate member. For example, the cavity may be or include a through-hole(s) 246 shaped in correspondence with at least a portion of the perimeter of the orthopedic implant/retainer. Alternatively, or in addition, the cavity may be or include one or more recesses 248 defined in the inner face of internal portion 202 and configured to receive at least a portion of the orthopedic implant. For example, here, recesses 248 are structured to receive regions of wire 62. Alternatively, or in addition, a recessed portion of inner face 238 may receive any suitable portion of an implant/plate member, such that internal portion 202 extends over none or over any suitable portion of the outer face of the implant/plate member. In some embodiments, internal portion 202 may include a pair of narrow strips 250, 252 that flank through-hole 246 and that extend from leading region 210 to trailing region 214 of internal portion 202.

Figure 14:
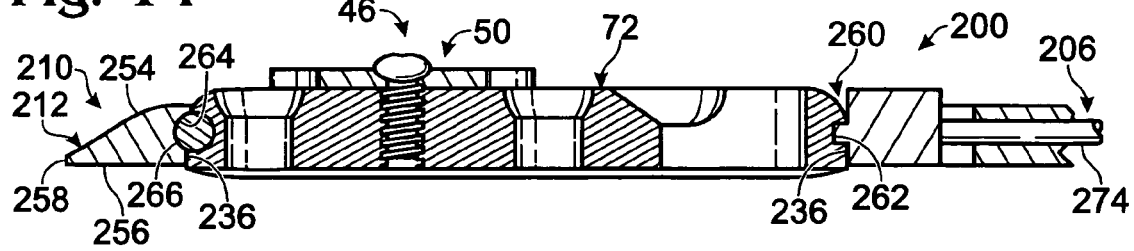
FIG. 14 is a sectional view of the fixation device and insertion tool of FIG. 12, taken generally along line 14-14 of FIG. 12.

FIG. 14 shows a sectional view of insertion tool 200 and device 46 coupled to one another. Blade structure 212 may be defined at least in part by a beveled outer surface 254 of leading region 210. The beveled outer surface may have a linear, concave, and/or convex profile and may extend toward inner surface 256 of leading region 210 to form a leading edge 258 that is sharp or dull. Leading region 210 may extend any suitable distance forward of the receiver structure/cavity, such as about less than about one-half or less than about one-fourth the length of the receiver structure/cavity.

Cavity 236 may be flanked by retention structure that holds an orthopedic implant in place during installation of the orthopedic implant under soft tissue and onto bone. The retention structure may be disposed on opposing sides of the cavity and/or at opposing ends, among others. The retention structure may include a projection(s) and/or a recess(es) that are complementary to a corresponding recess(es) and/or projection(s) of the orthopedic implant. For example, here, the retention structure includes a releasable detent 260 included in coupling mechanism 206. The detent may be received in a recess 262 formed in the trailing end of base plate 72 (and/or a bone plate). The detent may be biased toward the recess, such as via a spring, or may be locked in position against the recess, such as via threaded engagement with the base plate and/or within the coupling mechanism, among others. In any event, the detent may cooperate with opposing retention structure of the implant and the insertion tool to restrict removal of the implant from tool 200. For example, the opposing end of cavity 236 may include a projection received in a recess formed in the end of the implant or may include a recess 264 that receives a projection 266 provided by the implant (e.g., here, provided by the wire).

Coupling mechanism 206 may be operated to release the implant from tool 200, for example, after the implant is properly positioned on bone and under soft tissue, and, optionally, after the implant is secured to bone with fasteners. In particular, the coupling mechanism may be adjusted by hand via a user control (a release mechanism) 270 (FIG. 13) that remains outside the implant recipient with the implant disposed under soft tissue. The user control may be configured to be engaged and operated by hand and thus may include, for example, a knob 272, a lever, a button, and/or the like. Alternatively, the coupling mechanism may be adjusted for release of the implant with another instrument. Here, knob 272 is connected to detent 260 via a shaft 274. According to the nature of the coupling mechanism, the knob may, for example, be turned and/or urged away from internal portion 202, among others, to release engagement of detent 260 with the implant. With the detent released, internal portion 202 may be uncoupled and separated from the implant by urging the internal portion outward from bone such that the tool is generally above the implant. The internal portion then may be retracted over the implant and out through the incision for removal of the tool from the implant recipient.

IV. Spanning Elements

The systems and/or devices of the present disclosure may include one or more spanning elements that provide at least a pair of spanning members in the form of slender bars or rods (termed wire body portions, wire segments, or shafts) for spanning a bone discontinuity at least twice. Each spanning element may have any suitable shape, size, surface structure, and/or openings, among others.

The spanning element may be shaped for orthopedic use. Accordingly, the spanning element may have at least a portion that is shaped according to a target region of bone over/onto which the spanning element will be placed. The spanning element may be pre-shaped, that is, shaped during manufacture (i.e., before use) according to a target region of bone. The at least a portion of the spanning element may have a longitudinal and/or transverse shape that matches a contour(s) of the target region of bone. For example, the at least a portion of the spanning element may extend nonlinearly along the target region, which may keep the portion of the spanning element near and/or in contact with the bone and reduce the spanning element's profile above the bone's surface. Any suitable portion of the spanning element may be shaped according to a target region of bone, such as at least most or substantially all of the spanning element and/or least one or more spanning members thereof. In some embodiments, a portion of the spanning element for placement closer to an end of a target bone may be shaped according to a target region, and another portion of the spanning element for placement closer to a longitudinal center and/or shaft of the bone may be shaped according to a plate member that will at least partially receive the other portion of the spanning element and/or that will be used to secure one of the opposing ends of the spanning element to bone. In some embodiments, the spanning element may include at least one substantially linear region and one or more nonlinear regions or bent regions.

The spanning element may be configured to span a discontinuity in bone any suitable number of times. If configured to span the discontinuity only once, the spanning element may have an extended configuration in which the spanning element extends mostly in only one general direction and does not bend back on itself (e.g., see Section X, Example 3 below). If configured to span the discontinuity two or more times, the spanning element may bend back on itself one or more times to, for example, form a generally U-shaped (or O-shaped) or S-shaped spanning element, among others, that respectively spans the discontinuity exactly two or three times. The spanning element may bend back on itself smoothly, to form an arcuate end region (e.g., see FIG. 2), may bend back on itself sharply, to form an angular end region, or a combination thereof. If the spanning element bends back on itself, the spanning element may form an open loop (e.g., a U-shape) or may form a closed-loop (e.g., generally in an O-shape). If the spanning element forms a closed-loop, the closed-loop may, for example, be polygonal (e.g., rectangular), oval, or a combination thereof, among others. The spanning element may bend back on itself to provide at least a pair of fingers (spanning members) with any suitable lateral spacing. Lateral spacing between the fingers may be generally uniform (e.g., if the fingers are parallel and linear) or may vary along the fingers. In some embodiments, the spacing may generally increase (or decrease) as the fingers extend away from a bent region of the spanning element that connects the fingers, such as to give the spanning element a flared (or tapered) shape as the spanning element extends from the bent region. The spanning element may have any suitable cross-sectional shape that provides one or more wire segments that function as spanning members, such as circular, elliptical, polygonal, and/or the like.

The spanning element may have any suitable size. The collective length of the spanning element, as measured between opposing ends of the spanning element considered as a unit, may be any suitable fraction of the length of a target bone onto which the spanning element is to be placed, such as less than about one-half, or less than about one-fourth of the target bone's length, or a least about one-tenth of the target bone's length. The length of the spanning element may correspond to a characteristic dimension of the spanning element measured generally parallel to the fingers of the spanning element, among others. The overall width of the spanning element may be comparable to its thickness, if the spanning element does not bend back on itself, or the overall width of the spanning element may be defined collectively by the spanning element's fingers if the spanning element does bend back on itself. Furthermore, if the spanning element bends back on itself, the overall width of the spanning element may be uniform or may vary according to the shape and relative disposition of the spanning element's fingers. In some embodiments, the spanning element may be widest near one of the opposing ends of the spanning element, such as an end of the spanning element where the spanning element's fingers are not connected and/or an end of the spanning element configured to be disposed closer to an end of a bone.

The spanning element (and/or a wire body portion thereof) may have any suitable transverse dimension(s) locally. For example, the wire body portion may have a local diameter/width/thickness selected according to a desired flexibility/rigidity of the wire body portion and/or to maintain a low profile of the wire body portion above bone. The diameter, width, and/or thickness of the wire body portion may be substantially uniform or may vary along the wire body portion. A varying transverse dimension may provide an altered flexibility along the wire body portion, such as to determine where the wire body portion needs to be more rigid or more flexible. A local transverse dimension of the spanning element also may increase in one or more discrete regions along the spanning element where the spanning element defines openings. The discrete regions defining openings also may be wider, to provide a more plate-like structure, such as a head.

The spanning element may have any suitable number, shape, and position of openings for receiving fasteners. The spanning element may have only one opening, at least a pair of openings, exactly two openings, or three or more openings, among others. Each opening may be circular or elongate, among others. The opening may be completely or at least mostly enclosed by a circumferential wall. In addition, the opening may have a uniform diameter through the opening or may taper or flare toward the inner side of the opening. The opening may have or lack a countersink structure. Furthermore, the opening may have a smooth wall or may include structure, such as an internal thread, for retaining and/or locking a threaded fastener to the spanning element. The opening(s) may be disposed near only one of the opposing ends of the spanning element's body or may be a plurality of openings collectively disposed near both of the opposing ends. If the openings are disposed collectively near both opposing ends, in some embodiments, the spanning element may be secured to bone with only fasteners and thus without the use of a plate member.

The spanning element may be formed by any suitable method. In some embodiments, the spanning element may include a body and one or more heads formed by distinct components. The heads may be attached to the body by any suitable approach, such as by welding, with an adhesive, by crimping, threaded engagement, a friction fit, etc. In some embodiments, the spanning element may be formed from a monolithic structure having one or more flared ends (and/or widened intermediate regions) that are shaped by forging to form heads in which openings may be created. In some embodiments, the spanning element and/or one or more spanning members may be formed from a plate by cutting the plate using an appropriate cutting technology, such as by wire electrical discharge machining (wire EDM), with a water jet, and/or using a saw, among others.

V. Plate Members

A system and/or device of the present disclosure optionally may include or use at least one plate member to connect a spanning element to bone via at least one fastener. The term "plate member," as used herein, generally refers to any structure or piece having a plate geometry (i.e., being at least mostly solid and having a width that is much greater than its thickness) and being configured to be attached to bone with the plate member at least mostly or completely under the skin. The plate member thus may be configured to reduce irritation to the bone and surrounding soft tissue. For example, the plate member may have a low and/or feathered profile to reduce its protrusion into overlying soft tissue and rounded, burr-free surfaces to reduce the effects of such protrusion. The plate member thus may be a washer, a bone plate, and/or any other plate-like structure for use on bone and may have any suitable shape, structure, and apertures, as described further below.

The plate members of the present disclosure may have any shape suitable for use on their intended target bones. The plate member may be shaped for use on any suitable bone or bones to be fixed, including a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, a skull, a mandible, and/or the like.

Each plate member may be configured for use on any suitable side or sides of the body. For example, the plate member may be configured for use on both the left side and right side of the body/skeleton, such as when the plate member is bilaterally symmetrical. Alternatively, each plate member may be configured for use on either the left side or right side of the body/skeleton, but not both.

Each plate member may have any suitable contour. In some examples, the plate member (or a base plate thereof) may be supplied in a pre-contoured configuration produced during plate manufacture (e.g., by pre-operative bending, molding, and/or machining, among others) to include an inner surface that is complementary to a nonplanar surface region of a target bone. The plate member thus may be pre-contoured according to an average or representative surface geometry of a target bone. Alternatively, or in addition, the plate member may be contoured peri-operatively (e.g., by deforming the plate member), to adjust its shape before and/or during its installation on bone, to improve, for example, the fit of the plate member on a target bone for particular individuals and/or on distinct regions of the target bone.

Each plate member may be generally elongate, with length L>width W>thickness T. In use, the long axis of the plate member may be aligned with the long axis of a target bone and/or may extend obliquely and/or transversely relative to the long axis. In some embodiments, the plate member may have a length and a width that are about the same.

Each plate member may be unitary (formed as one piece) or may include two or more discrete pieces. The two or more discrete pieces may be secured to one another or may be connected through a mechanical joint that enables translational and/or pivotal movement to adjust the shape and/or size of the plate member.

VI. Fasteners

Fasteners suitable for use with the fixation devices of the present disclosure generally comprise any mechanism for affixing a plate member and/or a spanning member to a bone, plate member components to one another, and/or a spanning element to a plate member. Exemplary fasteners include bone screws, pegs, or the like. The size and shape of the fasteners may be selected based on the openings/apertures of the plate member and spanning members and/or based on the site of installation on bone, among others.

Bone screws may include unicortical, bicortical, and/or cancellous bone screws. Unicortical and bicortical bone screws typically have relatively small threads (shallower and/or a smaller pitch) for use in hard bone, such as is typically found in the shaft portion of a long bone, whereas cancellous bone screws typically have relatively larger threads (deeper and/or a larger pitch) for use in soft bone, such as is typically found near the ends (metaphyseal regions) of a long bone. Unicortical bone screws penetrate the bone cortex once, adjacent the site of insertion, whereas bicortical bone screws penetrate the bone cortex twice, once adjacent the site of insertion and again opposite the site of insertion. Generally, unicortical screws provide less support than bicortical screws, because they penetrate less cortex.

In some embodiments, each fastener placed into an opening/aperture of a fixation device may be a locking fastener that engages and locks to the fixation device, to restrict axial motion of the fastener. For example, the locking fastener may have at least one external thread for threaded engagement with the fixation device. The external thread may be formed on a shaft and/or a head of the fastener. The external thread may be one thread (single-threaded) or a plurality of threads (e.g., double-threaded, triple-threaded, etc.). The threads may be interspersed, so that the shaft is multi-threaded with a plurality of thread leads, for example, to accommodate a greater pitch (a steeper thread angle). Alternatively, or in addition, the threads may be disposed on adjacent and/or nonoverlapping regions of the shaft and/or head. The pitch of a thread may be constant along the shaft/head, or may change either continuously or discontinuously according to position. For example, the pitch may decrease (or increase) toward a head of the fastener, to provide compression (or distraction) of the bone as the fastener is advanced into the bone. In some embodiments, the external thread may be two or more discrete threads with different pitches, such as a leading thread with a greater pitch, and a trailing thread with a lesser pitch, or vice versa.

In some embodiments, the thread of a locking fastener may have an at least substantially constant pitch along the shaft of the fastener. In these embodiments, the rate of advancement of the threaded shaft into bone may be at least substantially equal to the rate of advancement of the threaded shaft through a locking opening/aperture of the fixation device, to restrict compression of the fixation device against the bone and to preserve any desired spacing between the fixation device and the bone as the locking fastener is fully advanced into the opening/aperture. The structure of a thread on a threaded shaft may be selected according to a locking opening/aperture into which the fastener is to be threaded.

VII. Composition of System Components

The fixation devices, associated fasteners, and/or any other system components disclosed herein may be formed of any suitable biocompatible material(s) and/or bioresorbable (bioabsorbable) material(s). Illustrative biocompatible materials that may be suitable for a spanning member, plate member, and/or other system component include (1) metal (for example, titanium or titanium alloy, cobalt-chrome alloy, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramic (for example, alumina, beryllia, calcium phosphate, and/or zirconia, among others); (4) composite (for example, carbon-fiber composites); (5) bioresorbable material or polymer (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone material or bone-like material (e.g., bone chips, calcium phosphate crystals (e.g., hydroxyapatite, carbonated apatite, etc.)); and/or the like.

The pieces of a multi-piece fixation device may be formed of the same or different materials. For example, the pieces each may be formed of metal, of the same or different composition, or one or more (or all) of the pieces may be formed of a non-metal material, such as a plastic, ceramic, and/or bioresorbable material.

VIII. Methods of Fixing Bones

The present disclosure provides methods of fixing bones with at least a pair of slender spanning members spanning a fracture outside of bone. The methods may include any of the steps presented below or elsewhere in the present disclosure. The steps may be performed in any suitable order, in any suitable combination, and each step may be performed any suitable number of times.

A bone may be selected for fixation. Any suitable bone (or bones for a fusion procedure) may be selected. Accordingly, the bone may be a long bone or another bone of the skeleton. The bone selected may be a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, and/or the like.

The selected bone may have a discontinuity. The discontinuity may be a pre-existing discontinuity present before surgery and/or a discontinuity introduced during performance of a method of bone fixation. Accordingly, the method may include a step of introducing a discontinuity into the selected bone, such as by cutting or breaking the bone. The bone may have any suitable condition to be treated, including a fracture, a cut, a malunion, a nonunion, a structural weakness, an undesirable length and/or angulation, and/or the like. The condition may affect any suitable portion of the bone, such as a diaphyseal (shaft or central) and/or a metaphyseal (end) region of the bone (e.g., a proximal or distal end region of a long bone). In exemplary embodiments, the selected bone region may be a proximal humerus, a distal radius, or a distal tibia with at least one metaphyseal fracture or with only one metaphyseal fracture.

In some embodiments, the method may include creating an incision through skin/soft tissue to access the bone. The step of creating an incision may create one or more incisions at any suitable position(s) relative to the selected bone. For example, an incision may be created longitudinally near an end of a bone (e.g., the proximal end or the distal end of the bone) or more centrally along the bone. In any event, the incision may be substantially shorter than the fixation device to be installed or may be about the same length as or longer than the device. Optionally, and particularly if the incision is substantially shorter than the orthopedic implant, at least a second incision may be created through skin/soft tissue to access the bone. The second incision also may be substantially shorter than the length of the orthopedic implant. In addition, the second incision may be disposed more centrally along the bone and/or more toward an end of the bone than the first incision. Each incision (or only one incision) may be created to access any suitable side of the selected bone, such as the anterior, posterior, medial, and/or lateral side of the bone. These and other suitable steps of the methods may be performed under sterile conditions and/or in a sterile field, for example, during surgery in an operating room.

A fixation device may be selected. Selection of a fixation device may include selecting at least one spanning element or a pair of spanning members and a plate member for use with the spanning element/spanning members. The step of selecting a fixation device may be based on the bone selected for fixation, for example, based on the type of bone, left/right sidedness of the bone, and/or the target region within the bone for fixation. Accordingly, the step of selecting a fixation device may include selecting a spanning element/members and/or a plate member that is sized and/or shaped according to the bone/bone region selected. For example, at least a portion of the spanning element/members and/or plate member may have a nonplanar inner surface (or inner face) and/or a bent configuration that is substantially complementary to and/or that substantially matches a surface region and/or a contour of the bone selected.

The fixation device may be disposed on the bone. Disposing the fixation device on bone may include placing the fixation device through an incision. In some embodiments, the fixation device may be advanced along an exterior surface of the bone from the incision such that at least a portion, at least most, or all of the fixation device is nonoverlapping with and/or spaced from the incision. Advancement of the fixation device may include moving the fixation device in any suitable direction with respect to bone, such as longitudinally and/or transversely, among others. If the fixation device is moved longitudinally, movement may be toward a central region of the bone and/or toward an end region of the bone, and either proximally or distally along the bone. Advancement of the fixation device may include advancing a spanning element/members, a plate member, and/or a wire-plate assembly (as a pre-assembled or pre-formed unit) along the bone. In some embodiments, advancement of the fixation device may be performed with the fixation device (or one or more components thereof) coupled to an insertion tool (e.g., see Section III). In any event, the fixation device may be disposed to span a bone discontinuity one or more times. In some embodiments, the fixation device may be disposed to span a bone discontinuity at least twice using wire body portions of spanning members.

The fixation device may be attached and/or secured to the bone. Attaching the fixation device may be performed with any suitable fasteners, such as one or more threaded fasteners that extend through openings/apertures of the fixation device and into the bone for threaded engagement with the bone, fixation device, or both. If the fixation device is an assembly of discrete pieces, individual pieces may be attached to bone in any suitable order. For example, if the fixation device includes a spanning element and a plate member, at least a portion of the spanning element may be attached to bone before the plate member, or at least a portion of the plate member may be attached to bone before the spanning element. Attaching the fixation device to the bone may include adjusting the relative disposition of device pieces, such as adjusting the disposition of a spanning element relative to a plate member (e.g., see Section X, Example 1). Adjusting the disposition may compress (or distract) the bone longitudinally. In addition, attaching the fixation device may include attaching a cover plate to a base plate and/or tightening the cover plate against at least one spanning element and/or against the base plate after the base plate has been attached to the bone. Furthermore, attaching the fixation device may include attaching at least one spanning element only with fasteners or attaching at least one spanning element with one or more fasteners on one side of a bone discontinuity and with a plate member on the opposing side of the bone discontinuity.

Attaching/securing the fixation device may include forming holes in the bone for receiving fasteners. The holes may be formed by the fasteners themselves, such as by using self-drilling fasteners, or may be formed with a hole-forming tool (i.e., a drill). The path along which each hole is formed may be guided by a wire (a guide wire) extending through an opening/aperture of the fixation device. Alternatively, or in addition, the path may be defined by a guide device coupled to the fixation device. In some embodiments, the guide device may be provided by an insertion tool to which the fixation device is coupled (e.g., see Section III).

If the fixation device is installed with the aid of an insertion tool, as described in the present disclosure, the insertion tool may be uncoupled from the fixation device at any suitable time. For example, the insertion tool may be uncoupled before the fixation device is attached to bone or after the fixation device is partially or fully attached to the bone. The uncoupled insertion tool may be removed from an implant recipient by retracting the insertion tool through the same incision used for advancing the insertion tool into the implant recipient. Alternatively, the insertion tool, and particularly an internal portion of the insertion tool, may be removed by advancing the insertion tool through a distinct incision relative to the incision through which the insertion tool was introduced (e.g., after uncoupling the internal portion of the insertion tool from an external portion thereof).

IX. Kits for Fixing Bones

The fixation devices of the present disclosure, or any components thereof, may be provided in kits for bone fixation. The kits may include any combination of one or more spanning elements, one or more plate members, fasteners for the spanning elements and/or plate members, a guide device(s) for guiding hole formation/fastener placement, at least one insertion tool, a drill(s), a saw or related cutting tool, at least one tool for bending the spanning elements (or spanning members)(e.g., see Section X, Example 7), one or more compression-distraction devices, instructions for use, or any combination thereof. The spanning elements may include a left spanning element and a right spanning element for use on respective left and right bones, but not vice versa. Alternatively, or in addition, the spanning elements may include a set of spanning elements of different size and/or shape for use on different bones, on different regions of the same bone, and/or on different sizes of the same bone. Some or all of the components of each kit may be provided in a sterile condition, such as packaged in a sterile container.

X. Examples

The following examples describe selected aspects and embodiments of the present disclosure, particularly exemplary multi-spanning fixation devices with alternative structure and methods of using the fixation devices. These examples and the various features and aspects thereof are included for illustration and are not intended to define or limit the entire scope of the present disclosure. The various features and aspects of the following examples may be combined with one another and/or may be introduced into any of the other fixation devices of the present disclosure in any suitable combination.

Example 1

Wire-based Fixation with Compression

This example describes an exemplary wire-based fixation device that facilitates compression of a bone and also describes an exemplary method of effecting compression with a wire-based device; see FIGS. 15-19.

FIG. 15 shows selected aspects of another illustrative multi-spanning fixation system 300. Here, a wire-plate device 302 of the system is partially installed on bone 42 (humerus 44), which is divided into proximal and distal fragments 86, 88 by discontinuity 80 (fracture 82). Device 302 may include a plate member 304 coupled to a spanning element in the form of a wire 306. The device may be adjustable between configurations in which the wire is slidable or fixed with respect to plate member 304.

Plate member 304 may have any of the features described elsewhere in the present disclosure for plate members. For example, plate member 304 may be structured generally as described above for plate member 50 of wire-plate device 46 (e.g., see FIGS. 1-6). In particular, plate member 304 may include a base plate 308 and cover plate 74 coupled to the base plate by cover fastener 76. Base plate 308 and cover plate 74 may define laterally disposed passages 310, 312 for receiving segments of wire 306. However, base plate 308 may have an end region 314 that is distinct from that of base plate 72 (e.g., see FIG. 3). For example, end region 314 may be indented to form a gap 318 at the end of the base plate between the wire and the base plate.

Wire 306 may have any of the features of the spanning elements described elsewhere in the present disclosure. For example, wire 306 may be structured generally as described above for wire 62 of wire-plate device 46 (e.g., see FIGS. 1-6). However, wire 306 may have surface structure 320 on wire body portions 322, 324 that restricts slippage of the wire relative to plate member 304.

FIG. 15 shows wire-plate device 302 in an adjustable configuration before compression of humerus 44. The adjustable configuration may be produced by cover plate 74 being incompletely secured (or not installed) against base plate 308, such as by loosening or only partially tightening cover fastener 76. As a result, wire 306 may not be clamped tightly between the base plate and the cover plate. Linear regions of wire segments 322, 324 thus may be slidable longitudinally along respective passages 310, 312.

An adjustable spacer 326 may be disposed between wire 306 and base plate 308, particularly between a bent end region 328 of the wire and end region 314 of the base plate. Spacer 326 may be provided by, for example, a tool (e.g., a tool similar to a screwdriver) with a tip (e.g., an oval tip) that fits into gap 318.

FIG. 16 shows wire 306 being moved in relation to plate member 304 by pivotal motion, indicated at 332, of spacer 326. In particular, the spacer may be reoriented such that the size of gap 318 is increased. As a result, wire segments 322, 324 may slide along passages 310, 312 to urge distal fragment 88 toward proximal fragment 86, as indicated by arrows at 334, thereby compressing humerus 44 longitudinally (and decreasing a gap, if any, between bone fragments at the fracture site).

FIG. 17 shows installation of wire-plate device 302 being completed. Spacer 326, if provided by a distinct tool, may be removed, indicated at 336. In addition, cover fastener 76 may be tightened, indicated at 338, to restrict slippage of wire 306 relative to plate member 304. Moreover, oblique bone screw 98 may be placed through distal fragment 88 and across fracture 82, for threaded (or nonthreaded) engagement with proximal fragment 86. The use of bone screw 98 to span fracture 82 may further restrict any undesired distraction of the compressed bone.

FIG. 18 shows a sectional view of wire-plate device 302. Plate member 304 and wire 306 may have generally complementary surface structure to restrict slippage of the wire body portions along plate-defined passages, such as slippage of wire body portion 324 along passage 312. For example, wire 306 may have surface structure 320 formed by a plurality of transverse notches 340 arranged along each wire body portion. The notches may be formed on any suitable portion of each wire body portion, such as on an outer surface region 342 (adjacent cover plate 74), an inner surface region 344 (adjacent base plate 308), and/or on one or both opposing side surfaces 346, 348. Plate member 304 may include complementary projections and/or recesses for mating with surface structure 320 of wire 306. For example, here, base plate 308 provides a series of ridges 350 configured to be received in notches 340. In other embodiments, cover plate 74 alternatively or in addition may provide surface structure for engaging and restricting slippage of wire 306. The generally complementary surface structure of the plate member and the wire may be configured to selectively restrict longitudinal motion of the wire in only one of two opposing directions. For example, here, the generally complementary surface structure is shaped to selectively permit bone compression and to selectively restrict bone distraction. In other embodiments, longitudinal motion of the wire in both opposing directions may be permitted and restricted equally by the complementary surface structure. In some examples, engaged surfaces of the wire and plate member may be textured (e.g., rough), instead of or in addition to generally complementary, to restrict slippage.

FIG. 19 shows an alternative or additional mechanism for restricting slippage of wire 306 relative to plate member 304. Here, a more permanent spacer 360, such as a bone screw 362, is disposed in gap 318. Spacer 360 may be installed in place of temporary spacer 326 (see FIGS. 15 and 16), after spacer 326 is removed, or may be used instead of spacer 326, such as to drive movement of wire 306 relative to plate member 304 by installation of spacer 360. For example, spacer 360 may be tapered to operate as a wedge that widens gap 318 as the spacer is advanced into bone. Alternatively, or in addition, spacer 360 may have a laterally elongate and/or off-center head, such that the pivotal position of the head between the plate member and the wire determines the size of gap 318. In other embodiments, spacer 360 may be coupled to wire-plate device 304 without entering bone.

Example 2

Wire-based Fixation Device with Covered Fasteners

This example describes an exemplary wire-based fixation device with a cover plate that extends over fasteners; see FIGS. 20 and 21.

FIG. 20 shows selected aspects of yet another illustrative multi-spanning fixation system 380, with a fixation device 382 of the system secured to bone 42 (fractured left humerus 44) via fasteners. Device 382 may include any of the features described elsewhere in the present disclosure, such as including wire 62 and base plate 72 (e.g., see FIGS. 1-6). However, the device may have a cover plate 384 that is larger than cover plate 72. In particular, cover plate 384 may overlap and/or cover one or more or all of apertures 90-94 of base plate 72 (e.g., see FIG. 3). For example, cover plate 384 may extend over one or more of the base plate apertures to block outward travel of fasteners, thereby preventing the fasteners from backing out and protruding into overlying soft tissue.

FIG. 21 shows a sectional view of fixation system 380 in the absence of bone. Cover plate 384 may be placed over bone screws 98-102 after the bone screws are placed through base plate 72 and into bone. The cover plate may completely or partially cover each aperture and/or the head of each bone screw. In some embodiments, cover plate 384 may include one or more recesses 386 formed in an inner surface 388 of the cover plate to accommodate at least a portion of a fastener head, such as a head 390 of bone screw 98.

Example 3

Fixation Device with Wires Segments Under a Plate Member

This example describes an exemplary wire-based fixation device including a plate member disposed over wire segments such that the wire segments are clamped between the plate member and bone; see FIGS. 22 and 23.

FIG. 22 shows selected aspects of still another illustrative multi-spanning fixation system 400 disposed on bone 42

(fractured humerus 44). System 400 may include a fixation device 402 including a plate member 404 that holds spanning elements including wire segments 406, 408 against bone. Plate member 404 may define one or more apertures 410 for receiving fasteners 412 that extend through the apertures and into bone 42. In other embodiments, plate member 404 may be used with only one wire, such as wire 62 of FIG. 1 with a bent configuration that forms a pair of spanning members from the same wire.

FIG. 23 shows a sectional view of bone 42 and system 400. Wire segments 406, 408 may be engaged with and clamped between plate member 404 and an exterior surface region 414 of bone 42. Plate member 404 may define at least one or a pair of grooves 416, 418 or other receiver structure for receiving a portion of each wire segment (and/or a region of a wire body portion of a single wire).

Example 4

Fixation Device with Fastener Assembly

This example describes an exemplary wire-based fixation device with a wire secured to bone by a fastener assembly; see FIG. 24.

FIG. 24 shows a longitudinal sectional view of selected aspects of still yet another illustrative multi-spanning fixation system 430 fixing bone 42 (fractured left humerus 44). System 430 may include at least one wire 62 (e.g., see FIGS. 1 and 2) secured to bone via head 56 of the wire using a fastener assembly 432.

Fastener assembly 432 may include an inner fastener 434 and an outer fastener 436 that locks to the inner fastener. Inner fastener 434, also termed a receiver fastener, may be placed into bone, for example, threaded into bone via an external thread 437, to dispose an internally threaded bore 438 in bone 42. Bore 438 may have a thread structure that is complementary to an external thread 440 formed on outer fastener 436. Accordingly, the outer fastener may extend through opening 58 of wire 62 for threaded engagement with inner fastener 434. The outer fastener may be turned until a head 442 of the outer fastener bears against head 56 of the wire, to hold head 56 between the inner and outer fasteners.

Example 5

Fixation Device with a Wire Extending into Bone

This example describes an exemplary wire-based fixation device with a wire having an end region that extends into bone; see FIG. 25.

FIG. 25 shows a longitudinal sectional view of selected aspects of another illustrative multi-spanning fixation system 450 fixing bone 42 (fractured left humerus 44). System 450 may include a wire 452 with a tip portion 454 that extends into bone. The tip portion may be placed directly into bone or may be placed into a receiver 456. The receiver may have an external thread 458 or other bone engagement structure for anchoring the receiver in bone. Tip portion 454 may have surface structure, such as ridges/notches, that resists slippage from receiver 456. Alternatively, or in addition, a bore 460 of receiver 456 may include ridges/notches to resist slippage.

Example 6

One-Piece Fixation Devices

Figure 28:
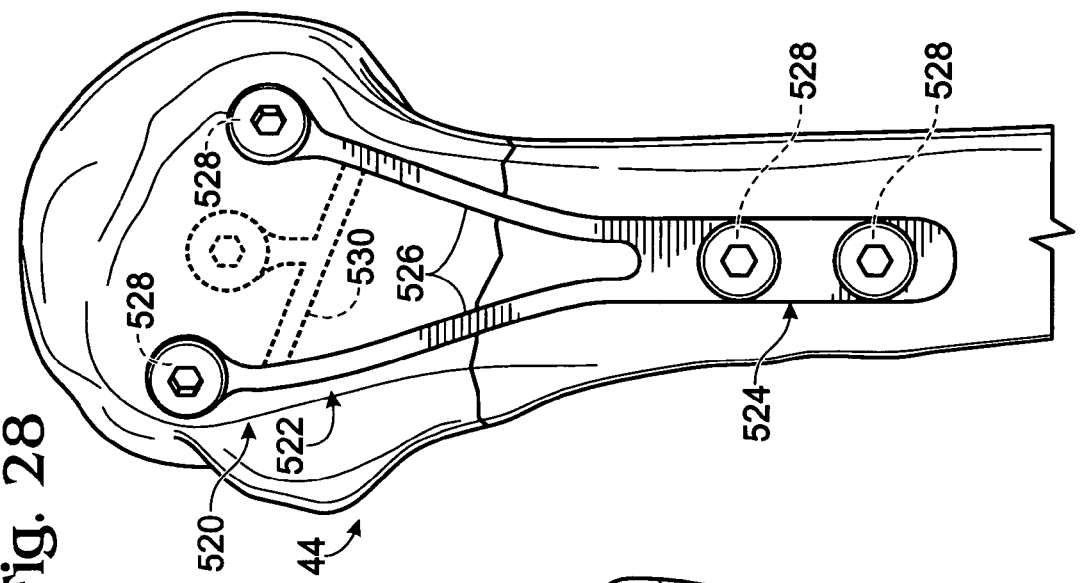
FIG. 28 is a view of the proximal portion of a fractured humerus being fixed with another exemplary multi-spanning fixation system that includes a one-piece fixation device, in accordance with aspects of the present disclosure.
Figure 27:
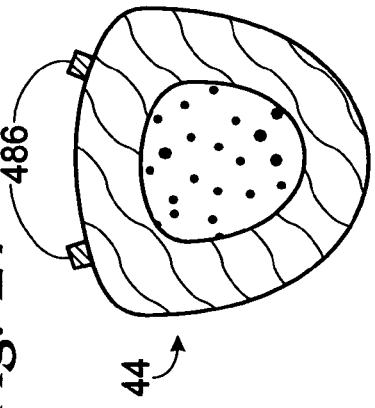
FIG. 27 is a sectional view of the humerus and fixation system of FIG. 26, taken generally along line 27-27 of FIG. 26.
Figure 26:
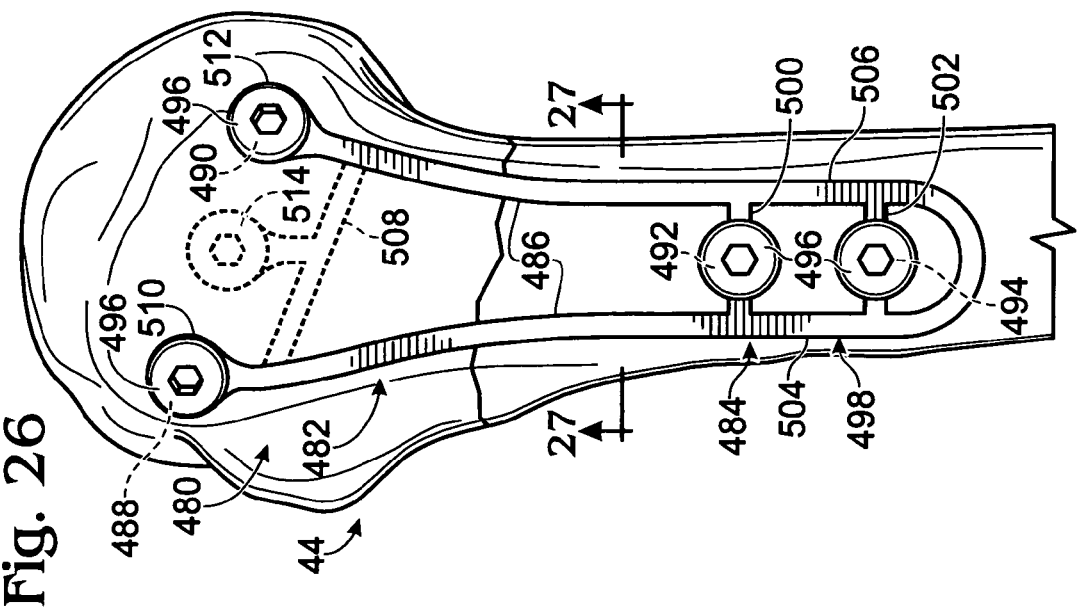
FIG. 26 is a view of the proximal portion of a fractured humerus being fixed with an exemplary multi-spanning fixation system that includes a unitary (one-piece) fixation device, in accordance with aspects of the present disclosure.

This example describes exemplary fixation systems that include a one-piece fixation device; see FIGS. 26-28.

FIG. 26 shows fractured humerus 44 being fixed with an exemplary multi-spanning fixation system 480 that includes a one-piece fixation device 482. Device 482 may include a frame 484 and at least a pair of slender spanning members 486 extending from the frame and disposed laterally of one another, for example, spaced from each other as shown here. Both the frame and the spanning members may define one or more openings 488-494 for receiving fasteners 496 that extend through the openings and secure the fixation device to bone. Spanning members 486 may include wire body portions having any suitable cross-sectional shape, such as the generally rectangular shape shown in FIG. 27, which optionally may include rounded corners.

Frame 484 may include a bent backbone 498 that extends to become spanning members 486, and one or more cross members 500, 502 that span lateral segments 504, 506 of the backbone. The cross members and the backbone may be part of the same monolithic structure or the cross members may be separate components that are attached to the backbone after they are formed.

In some embodiments, the fixation device may include a cross member 508 that connects spanning members 486 near their ends, or at least on an opposing side of the fracture from frame 484. For example, cross member 508 may extend between the spanning members adjacent heads 510, 512 of the spanning members. Cross member 508 thus may stabilize the spacing between the spanning members, effectively by extending the longitudinal extent of frame 484. Alternatively, or in addition, cross member 508 may contribute at least one opening 514, such as formed by a widened region or head of the cross member.

FIG. 28 shows humerus 44 being fixed with another exemplary multi-spanning fixation system 520 that includes a one-piece fixation device 522. Fixation device 522 may be generally Y-shaped and may include a plate member 524 and at least a pair of spanning members 526 extending generally longitudinally from the plate member. Plate member 524 and spanning members 526 each may define one or more openings 528 for receiving fasteners. Spanning members 526 may be connected to each other only via plate member 524 or also may be connected by a cross member 530.

Example 7

Spanning Member with Auxiliary Opening

This example describes an exemplary fixation system that includes a fixation device having a spanning member defining a primary opening for receiving a fastener and an auxiliary opening for receiving a tool; see FIGS. 29-31.

FIGS. 29 and 30 show fragmentary front and side views, respectively, of an exemplary fixation device 550, particularly an end region of a spanning member 552 thereof. The end region of the spanning member may define at least two openings, namely, a primary opening 554 sized to receive a fastener, such as a bone screw, and an auxiliary opening 556, which may be substantially smaller in size than the primary opening. The auxiliary opening may have any suitable position relative to the primary opening. For example, the primary opening may (or may not) be closer to an end of the spanning member than the auxiliary opening. In addition, the auxiliary opening may be defined by any suitable portion of the spanning member. In particular, the auxiliary opening may be defined near an end of the spanning member by a head 558, a neck 560, or a wire body portion 562 of the spanning member. Here, the auxiliary opening is defined by neck 560, which positions the auxiliary opening closer to a plate member of the device without weakening the wire body portion of the spanning member. Head 558 and/or neck 560 may be joined seamlessly to wire body portion 562 or may be provided by a discrete headpiece 564 attached to discrete wire body portion 562. The headpiece may define a socket 566 sized to receive the end of the wire body portion, and then may be fixed on the wire body portion by bonding, crimping, welding, with an adhesive, or the like.

Primary opening 554 may have any suitable dimensions, whether or not an auxiliary opening is present. For example, the primary opening may have a diameter that is substantially larger than the width of the wall extending at least mostly around the primary opening, such as a least about 50% larger or at least about twice or three times as large. Alternatively, or in addition, the primary opening and/or the wall extending at least mostly around the primary opening may have a thickness and/or width that is substantially less than (or substantially greater than) the width and/or thickness of neck 560 and/or wire body portion 562.

FIG. 31 shows an exploded view of an assembly 570 including spanning member 552 and an exemplary positioning tool 572 (also termed a deforming tool). Tool 572 may be configured to be coupled to the spanning member via auxiliary opening 556, to permit the position (e.g., the angular orientation) of the head to be adjusted by using the tool to deform spanning member 552, such as by twisting and/or bending wire body portion 562 of the spanning member.

Tool 572 may include a tip 574 connected to a handle 576 via an elongate shaft 578. The tip may be sized to be received in auxiliary opening 556, and may be retained in the auxiliary opening by any suitable mechanism, such as a friction fit, threaded engagement, or the like. After coupling tool 572 to the spanning member, a surgeon may manually re-position the tool in an appropriate manner to introduce a desired change in the position of head 558, such as to move the head laterally and/or to orient the head flat on the bone, among others. The length of tool 572, handle 576, and/or shaft 578 may be substantially less than, about the same as, or substantially greater than the length of spanning member 552.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of fixing bone, comprising:
    selecting a bone having a discontinuity near an end of the bone;
    providing a fixation device including a plate member and a U-shaped spanning component connected to the plate member with a clamp of the plate member formed at least in part by an upper plate, a lower plate, and a locking screw, the spanning component having a pair of legs that are round in cross section and that overlap the plate member and extend axially from the plate member to a pair of heads each defining an opening, the clamp being adjustable between a first configuration that permits the spanning component to slide parallel to a long axis of the plate member and a second configuration that fixes the spanning component to the plate member;
    placing the fixation device as a unit through an incision and onto the bone such that each leg spans the discontinuity and the plate member is arranged longitudinally on the bone and on an opposite side of the discontinuity from the end of the bone and the pair of heads; and
    attaching the fixation device to the bone using fasteners placed into the bone through apertures of the lower plate that are not covered by the upper plate and through the opening of each head.

2. The method of claim 1, wherein the step of placing includes a step of moving the plate member longitudinally along the bone from the incision by manipulating an insertion tool that is attached to the fixation device before the step of placing.

3. The method of claim 2, wherein the insertion tool includes a guide portion, and wherein the step of attaching includes a step of advancing fasteners to the apertures of the lower plate along paths defined by the guide portion.

4. The method of claim 1, wherein the U-shaped spanning component has a junction region that extends from one leg to the other leg, and wherein the junction region and the legs have the same average diameter.

5. The method of claim 1, wherein the U-shaped spanning component has a junction region that extends from one leg to the other leg, and wherein the junction region is round in cross section.

6. The method of claim 1, wherein the U-shaped spanning component has a junction region that extends from one leg to the other leg, and wherein the junction region is connected to the bone only via the legs after the step of attaching.

7. The method of claim 1, wherein the step of attaching does not adjust a compression applied to the spanning component by the clamp.

8. The method of claim 1, wherein a compression applied to the spanning component by the clamp is adjustable after the step of attaching, while the fasteners placed through apertures of the lower plate remain stationary.

9. The method of claim 1, wherein the step of placing includes a step of advancing heads of fasteners into engagement with the lower plate.

10. The method of claim 1, wherein fasteners placed through apertures of the lower plate are threaded fasteners, further comprising a step of sliding the spanning component parallel to a long axis of the plate member after the step of attaching, without turning any of the threaded fasteners after the step of attaching.

11. The method of claim 1, further comprising a step of compressing the bone longitudinally with the fixation device, after the step of attaching, with the clamp loosened such that the spanning component is slidable along the plate member, and a step of tightening the clamp after the step of compressing such that the spanning component is fixed to the plate member.

12. A method of fixing bone, comprising:
    selecting a bone having a discontinuity near an end of the bone;
    providing a fixation device including a plate member and a U-shaped spanning component connected to the plate member with a clamp of the plate member, the spanning component having a pair of legs overlapping the plate member and extending axially from the plate member to a pair of heads each defining an opening;

placing the fixation device as a unit through an incision and onto the bone such that each leg spans the discontinuity and the plate member is arranged longitudinally on the bone; and attaching the fixation device to the bone using fasteners placed into the bone through apertures of the plate member and through the opening of each head, wherein the plate member includes a first plate disposed under a second plate, and wherein the fasteners extend through the first plate and not the second plate after the step of attaching.

13. The method of claim 12, wherein the step of placing includes a step of moving the plate member longitudinally along the bone from the incision by manipulating an insertion tool that is attached to the fixation device before the step of placing.

14. The method of claim 13, wherein the insertion tool includes a guide portion, and wherein the step of attaching includes a step of advancing fasteners to the apertures of the plate member along paths defined by the guide portion.

15. The method of claim 12, wherein the U-shaped spanning component has a junction region that extends from one leg to the other leg, and wherein the junction region and the legs have the same average diameter.

16. The method of claim 12, wherein the U-shaped spanning component has a junction region that extends from one leg to the other leg, and wherein the junction region is round in cross section.

17. The method of claim 12, wherein the U-shaped spanning component has a junction region that extends from one leg to the other leg, and wherein the junction region is connected to the bone only via the legs after the step of attaching.

18. The method of claim 12, wherein the step of attaching does not adjust a compression applied to the spanning component by the clamp.

19. The method of claim 12, wherein a compression applied to the spanning component by the clamp is adjustable after the step of attaching, while the fasteners placed through apertures of the plate member remain stationary.

20. The method of claim 12, wherein the step of placing includes a step of advancing heads of fasteners into engagement with the first plate.

21. The method of claim 12, wherein fasteners placed through apertures of the plate member are threaded fasteners, further comprising a step of sliding the spanning component parallel to a long axis of the plate member after the step of attaching, without turning any of the threaded fasteners after the step of attaching.

22. The method of claim 12, further comprising a step of compressing the bone longitudinally with the fixation device, after the step of attaching, with the clamp loosened such that the spanning component is slidable along the plate member, and a step of tightening the clamp such that the spanning component is fixed to the plate member.

* * * * *